US010208276B2

(12) United States Patent
Johnson

(10) Patent No.: US 10,208,276 B2
(45) Date of Patent: Feb. 19, 2019

(54) PURE ALGAE GROWTH SYSTEM AND METHOD

(71) Applicant: SIFTEX EQUIPMENT COMPANY, INC., South Windsor, CT (US)

(72) Inventor: Martin L. Johnson, Chester, VA (US)

(73) Assignee: SIFTEX EQUIPMENT COMPANY, INC., South Windsor, CT (US)

( * ) Notice: Subject to any disclaimer, the term of this patent is extended or adjusted under 35 U.S.C. 154(b) by 0 days.

(21) Appl. No.: 15/184,394

(22) Filed: Jun. 16, 2016

(65) Prior Publication Data

US 2018/0371391 A1    Dec. 27, 2018

Related U.S. Application Data

(60) Provisional application No. 62/230,850, filed on Jun. 17, 2015.

(51) Int. Cl.
   *C12M 1/12*   (2006.01)
   *C12M 1/00*   (2006.01)
   *C12M 1/02*   (2006.01)

(52) U.S. Cl.
   CPC ............ *C12M 23/06* (2013.01); *C12M 23/02* (2013.01); *C12M 23/22* (2013.01); *C12M 27/00* (2013.01); *C12M 39/00* (2013.01); *C12M 41/24* (2013.01)

(58) Field of Classification Search
   CPC ....................................................... C12M 1/12
   See application file for complete search history.

(56) References Cited

U.S. PATENT DOCUMENTS

| 8,476,067 B2 * | 7/2013 | Morgan ............... B01D 53/007 435/292.1 |
| 9,206,388 B1 * | 12/2015 | Collins .................... C12N 1/12 |
| 2009/0148927 A1 * | 6/2009 | Schroeder .............. A01G 33/00 435/257.1 |

OTHER PUBLICATIONS

Palmowski et al., Clean in Place—A Review of Current Technology and its Use in the Food and Beverage Industry, Deakin University, 2005, http://www.dmsc.com.au/dmsc/reports/Report_Clean-In-Place-review_Deakin-University.pdf.*
Bremer, Philip J. et al. Laboratory scale Clean-in-Place (CIP) studies on the effectiveness of different caustic and acid wash steps on the removal of dairy biofilms, *International Journal of Food Microbiology* 106 (2006) 254-262.

(Continued)

*Primary Examiner* — Rosanne Kosson
(74) *Attorney, Agent, or Firm* — Marianne Fuierer; Olive Law Group, PLLC

(57) ABSTRACT

A tank receives, mixes, and dispenses input materials including algae feed stock, a micro-nutrients, cleaning solution, a sterile gas, a heating/cooling fluid, carbon dioxide, and raw water with a water treatment system. A plurality of output stations include a vent to atmosphere, a heating/cooling media return, a cleaning disposal, and an algae concentrate/product. The vent to atmosphere is coupled to the tank. The heating/cooling media return is coupled to the heating/cooling media supply through the tank. The cleaning solution disposal station is coupled to the tank with a pump followed by a nano bubbler and an algae growing system. An algae concentrate/product station is coupled to the tank. An algae dewatering system is intermediate the tank and the algae concentrate/product. A water return line couples the algae dewatering system and the water treatment system.

14 Claims, 13 Drawing Sheets

(56) References Cited

OTHER PUBLICATIONS

Geigert, John et al. Role of Quality Control in Validation of Biopharmaceutical Processes: Case Example of Clean-in-Place (CIP) Procedure for a Bioreactor, *PDA Journal of Pharmaceutical Science & Technology*, 48 (1994) 236-240.

Myers, Ted et al. Approaches to Cycle Development for Clean-in-Place Processes, *Journal of Parenteral Science & Technology*, 41 (1987) 9-15.

Roy, Kevin et al. Multivariate Statistical Monitoring as Applied to Clean-in-Place (CIP) and Steam-in-Place (SIP) Operations in Biopharmaceutical Manufacturing, *Biotechnol Prog*, 30 (2014) 505-515.

* cited by examiner

FIG. 4

| LIGHT TRANSMISSION | STRENGTH | SUNLIGHT DEGRADATION | ROBUSTNESS | ON-SITE REPAIR |
|---|---|---|---|---|
| (Graph: I'/I vs T mm THICKNESS, 0 to 2.0; curve reaching ~1.0) | TUBULAR REACTOR (diagram with D = diameter, T = wall thickness, P = pressure) | (Graph: I'/I vs TIME, MONTHS; 5% LESS AFTER 6 MONTHS) | TYPICAL INSTALLATION (sun and hand icons) | SMALL PUNCTURE (circle diagram with P) |
| $I$ = INTENSITY OF LIGHT 300-750 NANOMETER WAVELENGTH | $\sigma = PD/T$ | TIME, MONTHS (IN OPERATION) $I$ = LIGHT INTENSITY $I'$ = LIGHT INTENSITY THRU MEMBRANE | ASSEMBLY (MUST RESIST): ABRASION; WIND BORNE SAND; TEMPERATURE CHANGE; CRIMPING; COMPRESSION (HEEL PRESS) | REPAIR CAPABILITY: SMALL PUNCTURES CAN BE REPAIRED WITH PLUG OR PATCH |
| $I'$ = INTENSITY THRU MEMBRANE | $\sigma$ = TENSILE STRESS; P = PRESSURE; D = DIAMETER; T = WALL THICKNESS | SEE FIG. 6 FOR MORE RIGOROUS TESTING | OPERATION (MUST RESIST): SUNLIGHT; TEMPERATURE CHANGE; WORKER ABUSE | : MAJOR FAILURES CAN BE REPAIRED WITH SLEEVE OR EQUIV. |
| | FOR TURBULENT FLOW AND TROPICAL LIGHT OPTIMAL D = 100mm | | | : ENTIRE "RUN" CAN BE REPLACED WHILE IN OPERATION |
| | o SYSTEM PRESSURE = 20PSIG<br>o WALL THICKNESS = 1mm<br>$\sigma$ = 20PSI * 100/1 = 2000LB/IN2<br>FOR SAFETY FACTOR OF 4 6 ULTIMATE = 8000PSI | | | |
| DESIGN CRITERIA 1mm WALL THKNS | DESIGN CRITERIA ULTIMATE TENSILE STRENGTH 8-10000 PSI | DESIGN CRITERIA MAXIMUM LOSS OF LIGHT TRANSMISSION 5% IN 6 MONTHS OPERATION | DESIGN CRITERIA SUITABLE FOR HANDLING BY WORKERS WITH MINIMAL FORMAL TRAINING | DESIGN CRITERIA ROBUST SYSTEM SUITABLE FOR INDUSTRIAL USE |

PURE ALGAE GROWTH SYSTEM AND METHOD

PRIORITY DATE

This application is based upon, and claims the priority of, provisional application No. 62/230,850, which was filed in the United States Patent and Trademark Office on 17 Jun. 2015, the disclosure of which is incorporated herein by reference.

BACKGROUND OF THE INVENTION

Field of the Invention

The present invention relates to a pure algae growth system and method and more particularly pertains to growing algae in a safe, convenient, and economical manner.

Description of the Prior Art

The use of algae growing devices is known in the prior art. More specifically, algae growing devices previously devised and utilized for the purpose of growing algae are known to consist basically of familiar, expected, and obvious structural configurations, notwithstanding the myriad of designs encompassed by the crowded prior art which has been developed for the fulfillment of countless objectives and requirements.

LITERATURE CITED

The following references and others cited herein but not listed here, to the extent that they provide exemplary procedural and other details supplementary to those set forth herein, are specifically incorporated herein by reference.

US Patent Documents

U.S. Pat. Nos. 4,253,271; 5,104,803; and 5,958,761

Other Patent Documents

WO00174990, WO1999046360

OTHER PUBLICATIONS

Chen C Y, Liu C H, Lo Y C, Chang J S. 2011. Perspectives on cultivation strategies and photobioreactor designs for photo-fermentative hydrogen production. Bioresource Technology 102:8484-8492

Feng P, Deng Z, Hu Z, Fan L. 2011. Lipid accumulation and growth of *Chlorella zofingiensis* in flat plate photobioreactors outdoors. Bioresource Technology 102:10577-10584

Feng P, Deng Z, Fan L, Hu Z. 2012. Lipid accumulation and growth characteristics of *Chlorella zofingiensis* under different nitrate and phosphate concentrations. Journal of Bioscience and Bioengineering 114:405-410

Pinker R T. 1995. Estimating Photosynthetically Active Radiation (PAR) at the earth's surface from satellite observations. Remote Sensing of Environment 51:98-107

Guil Guerrero J L, Rebolloso-Fuentes M. 2008. Nutrient composition of *Chlorella* spp. and *Monodus subterraneus* cultured in a bubble column reactor. Food Biotechnol 22:218-233

Hall D O, Fernandez F G, Guerrero E C, Rao K K, Grima E M. 2003. Outdoor helical tubular photobioreactors for microalgal production: modeling of fluid-dynamics and mass transfer and assessment of biomass productivity. Biotechnology and Bioengineering 82:62-73

Heinrich J M, Niizawa I, Botta F A, Trombert A R, Irazoqui H A. 2012. Analysis and design of photobioreactors for microalgae production II: experimental validation of a radiation field simulator based on a Monte Carlo algorithm. Photochemistry and Photobiology 88:952-960

Jung E E, Jain A, Voulis N, Doud D F, Angenent L T, Erickson D. 2014. Stacked optical waveguide photobioreactor for high density algal cultures. Bioresour Technol 171:495-499

Lane C, Hapel K, Rismani-Yazid H, Kessler B A, Moats K M, Park J, Schwenk J, White N M, Bakhit A, Allnutt F. 2014. Final Scientific/Technical Report—DOE Award DE-FE0001888 Beneficial CO2 capture in an integrated algal biorefinerry for renewable generation and transportation fuels. DOE-NETL Lee Y-K. 2001. Microalgal mass culture systems and methods: Their limitation and potential. J Appl Phycol 13:307-315

Perez M, Nolasco N, Vasavaa A, Johnson M, Kuehnle A. 2015. Algae-mediated valorization of industrial waste streams. Industrial Biotech 11:229-234

Priess M, Kowalski S. 2010. Algae and Biodiesel: Patenting Energized as Green Goes Commercial. J Comm Biotech Bioengeeering 16:293

Sato R, Maeda Y, Yoshino T, Tanaka T, Matsumoto M. 2014. Seasonal variation of biomass and oil production of the oleaginous diatom *Fistulifera* sp. in outdoor vertical bubble column and raceway-type bioreactors. Journal of bioscience and bioengineering 117:720-724

Sheehan J, Dunahay T, Benemann J R, Roessler P. 1998. A look back at the US Deptartment of Energy's Aquatic Species Program: Biodiesel from Algae. National Renewable Energy Laboratory Ugwu C U, Ogbonna J C, Tanaka H. 2002. Improvement of mass transfer characteristics and productivities of inclined tubular photobioreactors by installation of internal static mixers. Applied microbiology and biotechnology 58:600-607

Van Den Hoek C, Mann D G, Jahns H M 1995 Algae: An Introduction to Phycology. Cambridge University Press.

While known devices fulfill their respective, particular objectives and requirements, they do not describe a pure algae growth system and method that allows growing algae in a safe, convenient, and economical manner.

In this respect, the pure algae growth system and method according to the present invention substantially departs from the conventional concepts and designs of the prior art, and in doing so provides an apparatus primarily developed for the purpose of growing algae in a safe, convenient, and economical manner.

Therefore, it can be appreciated that there exists a continuing need for a new and improved pure algae growth system and method which can be used for growing algae in a safe, convenient, and economical manner. In this regard, the present invention substantially fulfills this need.

SUMMARY OF SUMMARY OF THE INVENTION

In view of the disadvantages inherent in the known types of algae growing devices now present in the prior art, the present invention provides an improved pure algae growth system and method. As such, the general purpose of the present invention, which will be described subsequently in greater detail, is to provide a new and improved pure algae growth system and method which has all the advantages of the prior art and none of the disadvantages.

To attain this, from a broad perspective, the present invention essentially comprises a tank for receiving, mixing, and dispensing input materials. The input materials include algae feed stock, a micro-nutrients supply, a cleaning solution, a sterile gas, a heating/cooling fluid, a carbon dioxide supply, and a raw water supply with a water treatment system. A plurality of output stations include a vent to atmosphere station, a heating/cooling media return station, a cleaning disposal station, and an algae concentrate/product station. The vent to atmosphere station is coupled to the tank. The heating/cooling media return station is coupled to the heating/cooling media supply through the tank. The cleaning solution disposal station is coupled to the tank with a pump followed by a nano-bubbler and an algae growing system. An algae concentrate/product station is coupled to the tank. An algae dewatering system is intermediate the tank and the algae concentrate/product station. A water return line couples the algae dewatering system and the water treatment system.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved pure algae growth system and method which has all of the advantages of the prior algae growing devices and none of the disadvantages.

It is another object of the present invention to provide a new and improved pure algae growth system and method which may be easily and efficiently manufactured and marketed.

It is a further object of the present invention to provide a new and improved pure algae growth system and method which is of durable and reliable constructions.

An even further object of the present invention is to provide a new and improved pure algae growth system and method which is susceptible of a low cost of manufacture with regard to both materials and labor, and which accordingly is then susceptible of low prices of sale to the consuming public, thereby making such pure algae growth system and method economically available.

Lastly, it is an object of the present invention to provide a pure algae growth system and method for generating pure algae therefrom. The feeding of the input materials and the generating of the pure algae is done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

The invention will be better understood and objects other than those set forth above will become apparent when consideration is given to the following detailed description thereof. Such description makes reference to the annexed drawings wherein:

BRIEF DESCRIPTION OF THE DRAWINGS

A better understanding of the exemplary embodiments of the invention will be had when reference is made to the accompanying drawings wherein.

The material outflows shown consist of: 1) a vent to the atmosphere containing the sterile inert gas blanket material which now contains water from evaporation via contact of the actual algae growing media; 2) the heating/cooling media which is recycled and tempered prior to its reintroduction (this is only a temporary flowing stream); 3) cleaning solution which must be processed prior to ultimate disposal (this is only a temporary flowing stream); and 4) the final micro algae product which has been concentrated to some level based on the actual operator's final customer specification. These systems are further described in component system drawings and specifications.

Figure 2:
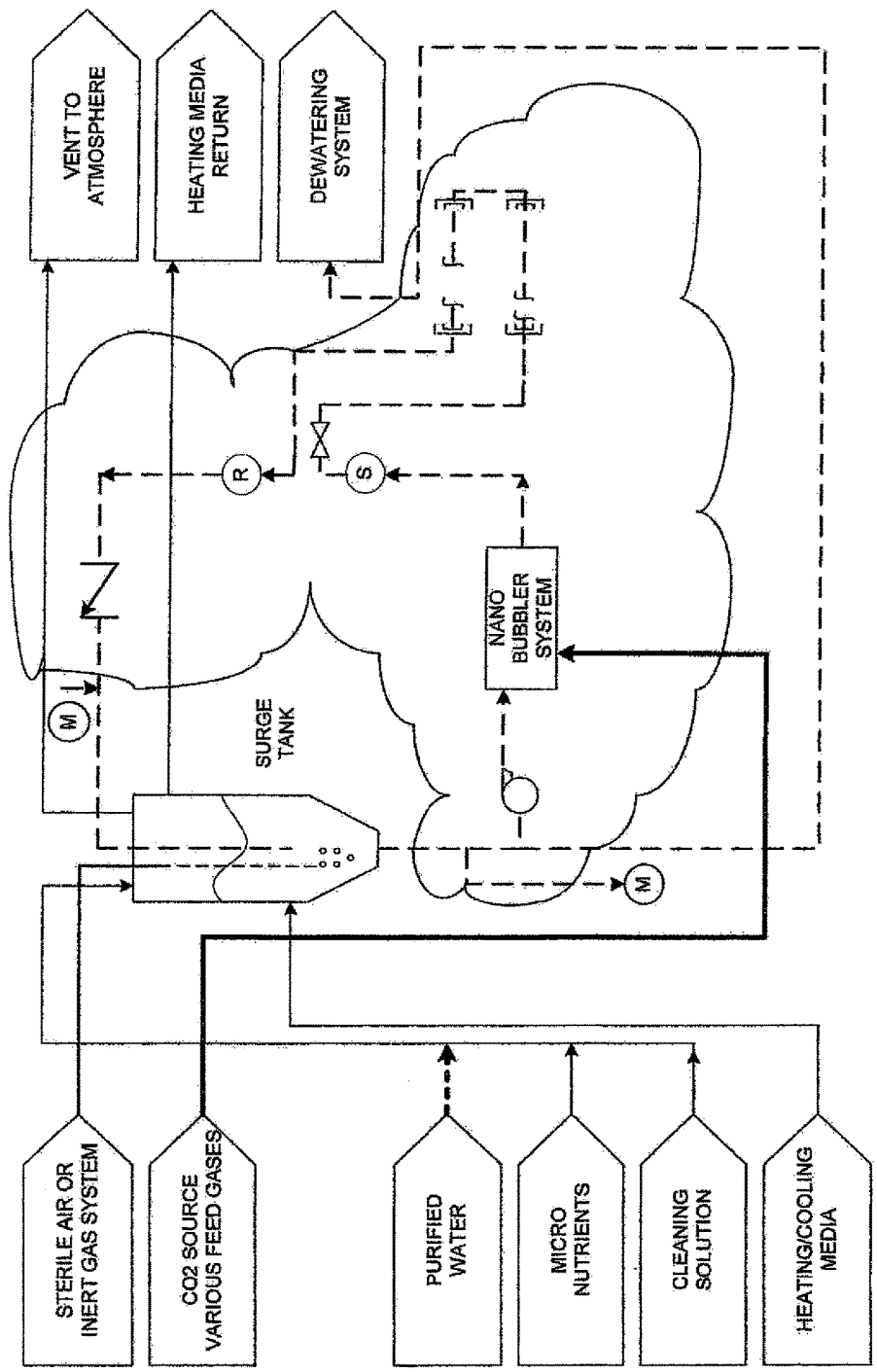

FIG. 2—Pure Algae Growth System Module. This displays an overall schematic of one possible configuration of the Pure Algae Growth Systems operating system. This configuration has ten actual photobioreactors. They exist as five "down and back" flow paths operated in a parallel manner. This feature allows the system to expand without the need of transferring to another physical location as the volume of the micro algae culture grows. These five flow paths make up one module and the supporting components of the system can accept as many as ten (total) of these modules using the same surge volume or tank and ancillary components. This feature provides significant economies of scale for the required component capital costs. This one module is also used as a base comparison for competing commercial system costs, both operating and capital.

Figure 3:
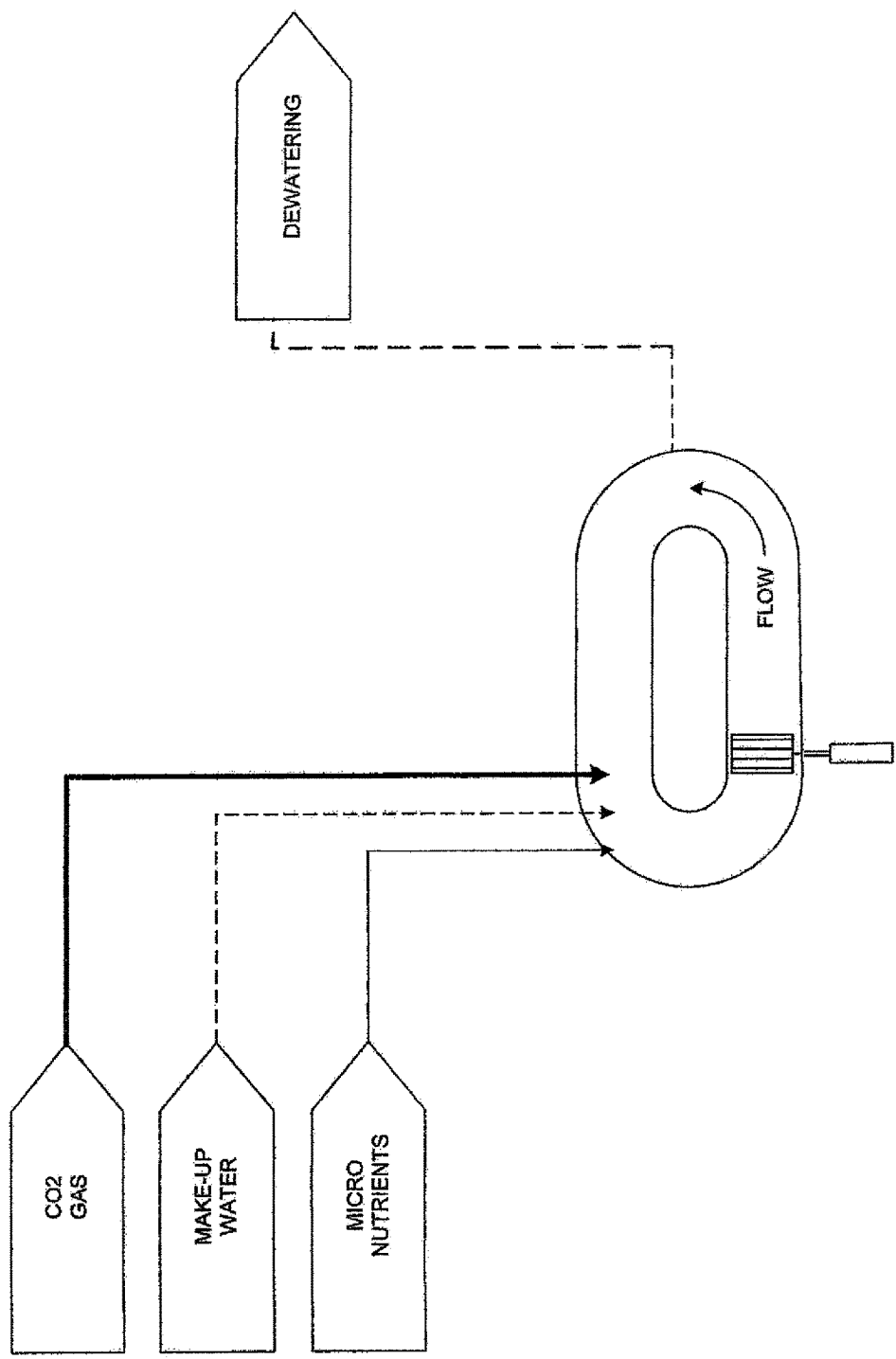

FIG. 3—Typical Commercial System. This displays an overall process schematic of a commercial raceway type micro algae growing system. This system is "sized" such that one such system can be harvested in a day and yield the equivalent amount of biomass (algae) as the Pure Algae Growth System which is described in FIG. 2 above. For equivalent yield (to an invention module), accounting for the necessary steps associated with a raceway type configuration, twenty-one actual raceway systems must be employed. This allows time for the necessary inoculation, growth, harvesting, and cleaning operations which must occur.

FIG. 4—Design criteria for acceptable tubular modular light reactors. The pressure exerted from the inside of the modular light reactors dictates the required tensile strength of the material used in their construction. The system is based on a nominal 100 millimeter diameter tube with a 1 millimeter wall thickness. The required media flow rates inside the tube result in a maximum pressure inside the tube of 20 lbs/square inch which requires a working tensile strength of 2,000 lbs/square inch.

Figure 5:
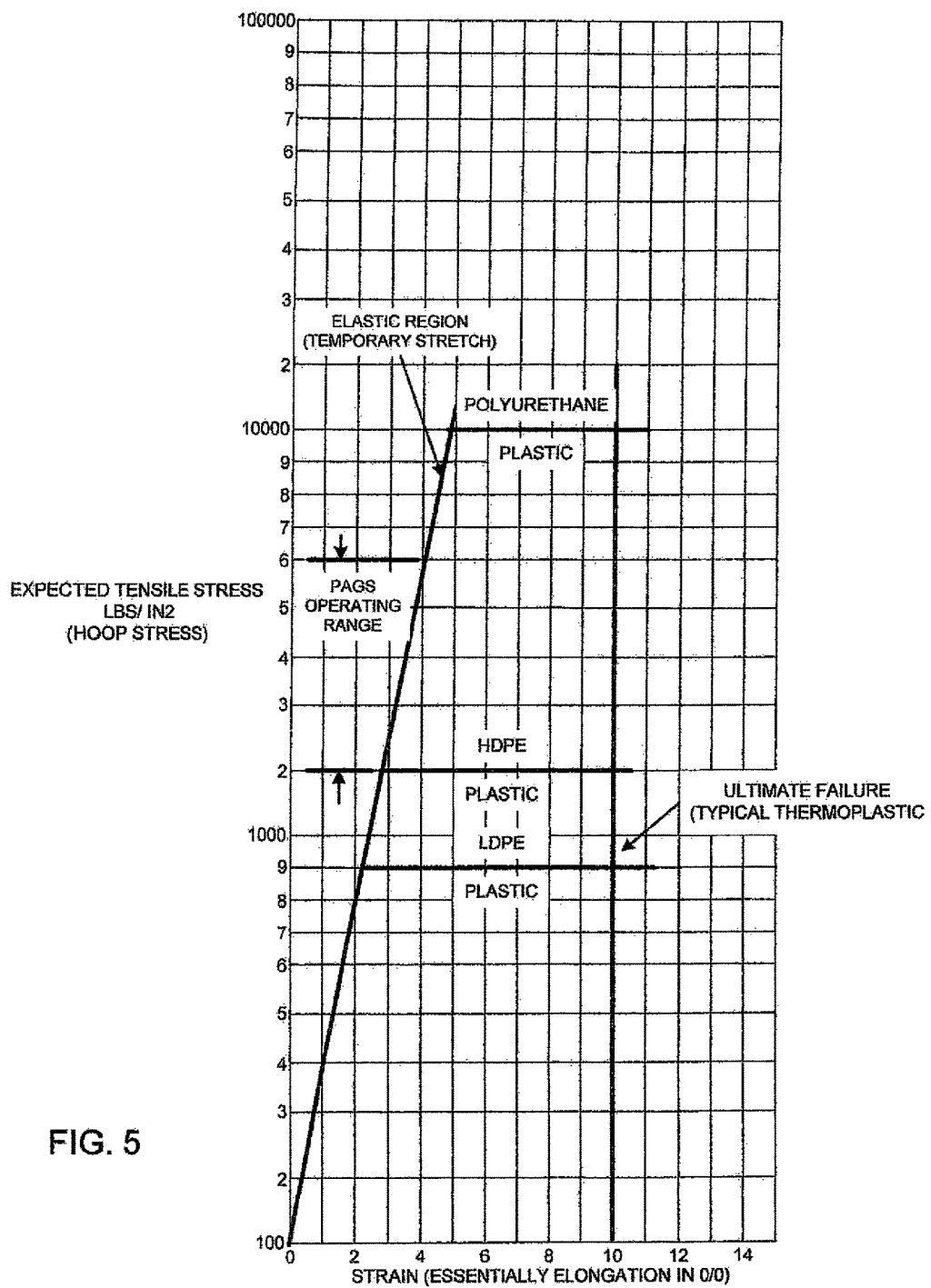

FIG. 5—Graphic Depiction. This is a semi-logarithmic graph displaying how various polymeric materials tolerate and respond to the internal pressure of the material flowing inside. This graph uses the 100 millimeter tube with a 1 millimeter wall thickness as an example and several commercially available polymeric materials stress tolerance are superimposed upon the graph. It provides the base design criteria outlined in FIG. 4 above and shows why the polyurethane polymer was chosen for the operating system.

Figure 6:
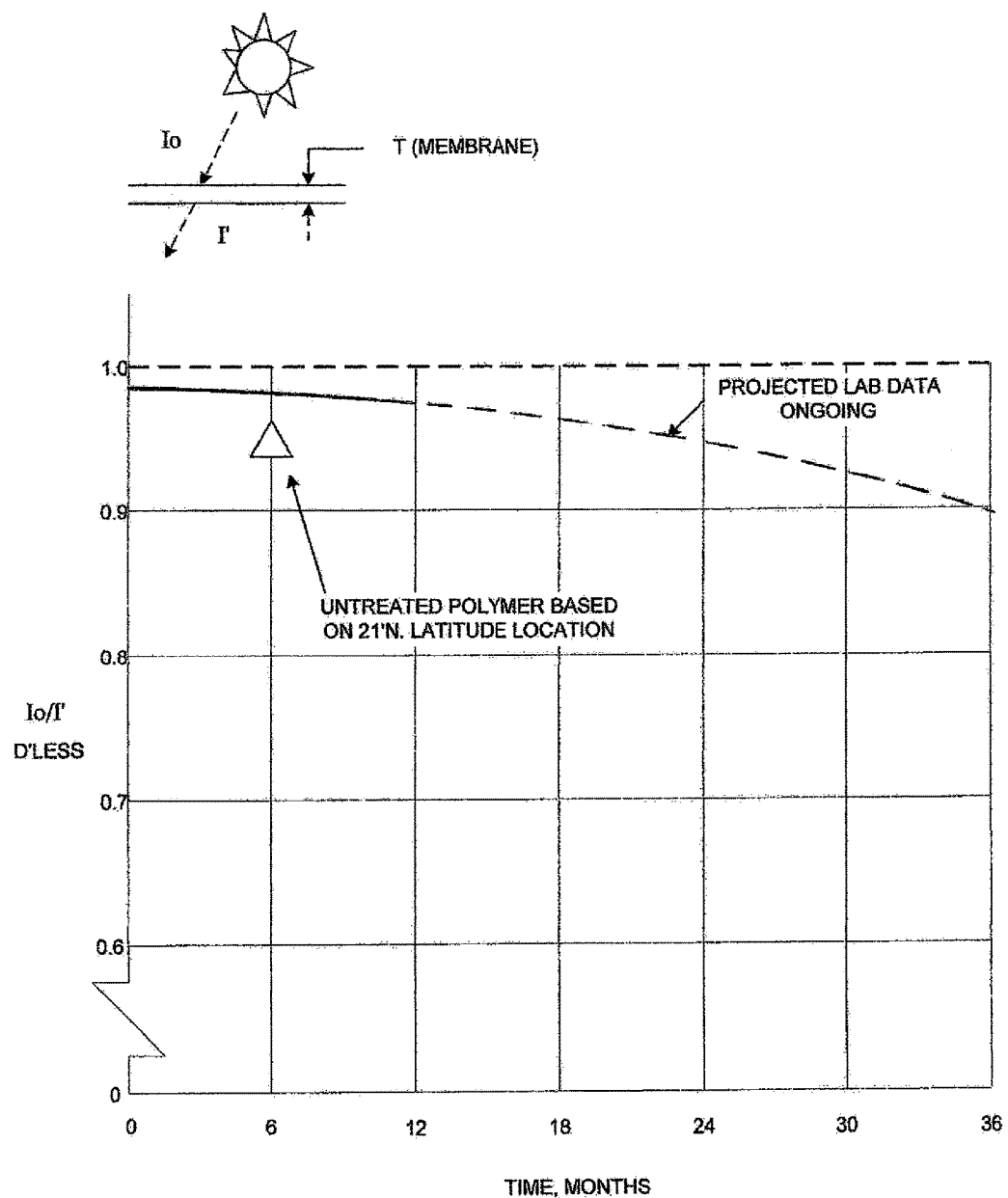

FIG. 6—Test Results. This displays the test results of 800 hours of heli-arc light exposure to polyurethane polymeric material which is to be used in the described invention. This test mimics the equivalent of sunlight in a tropical environment and is likely more severe than the actual real time use of the material in such an environment. This information substantiates the claim of long duration expected use of the polyurethane material in actual practice.

Figure 7:
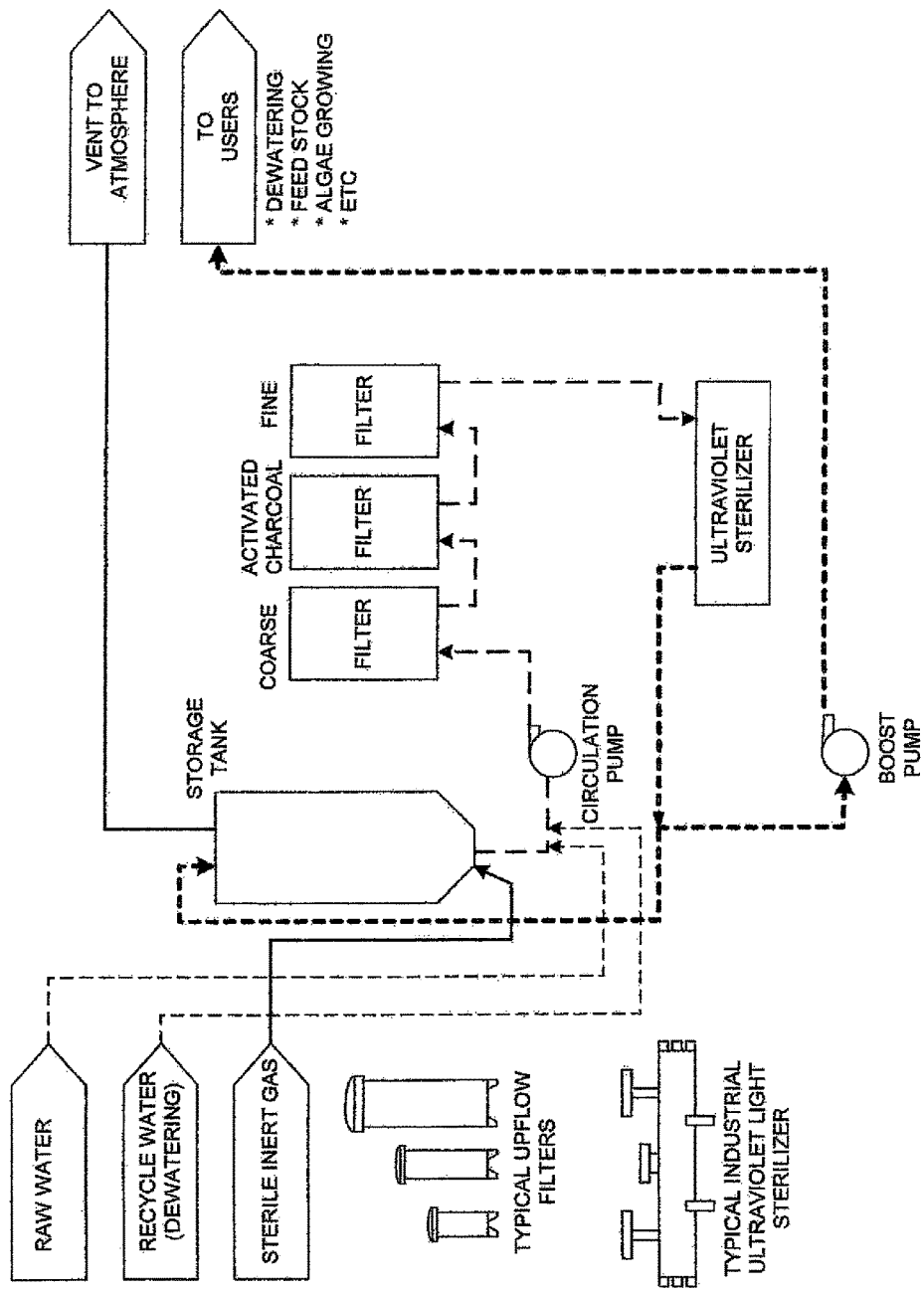

FIG. 7—Process Water System. This system shows how raw water is introduced and processed to the needed degree of cleanliness. This cleanliness factor ensures that foreign bodies or contaminants are kept out of contact with the algae. This cleaning operation consists of multiple filtrations followed by an ultra violet light sterilization treatment. All water that enters the system is treated prior to actual use.

Figure 8:
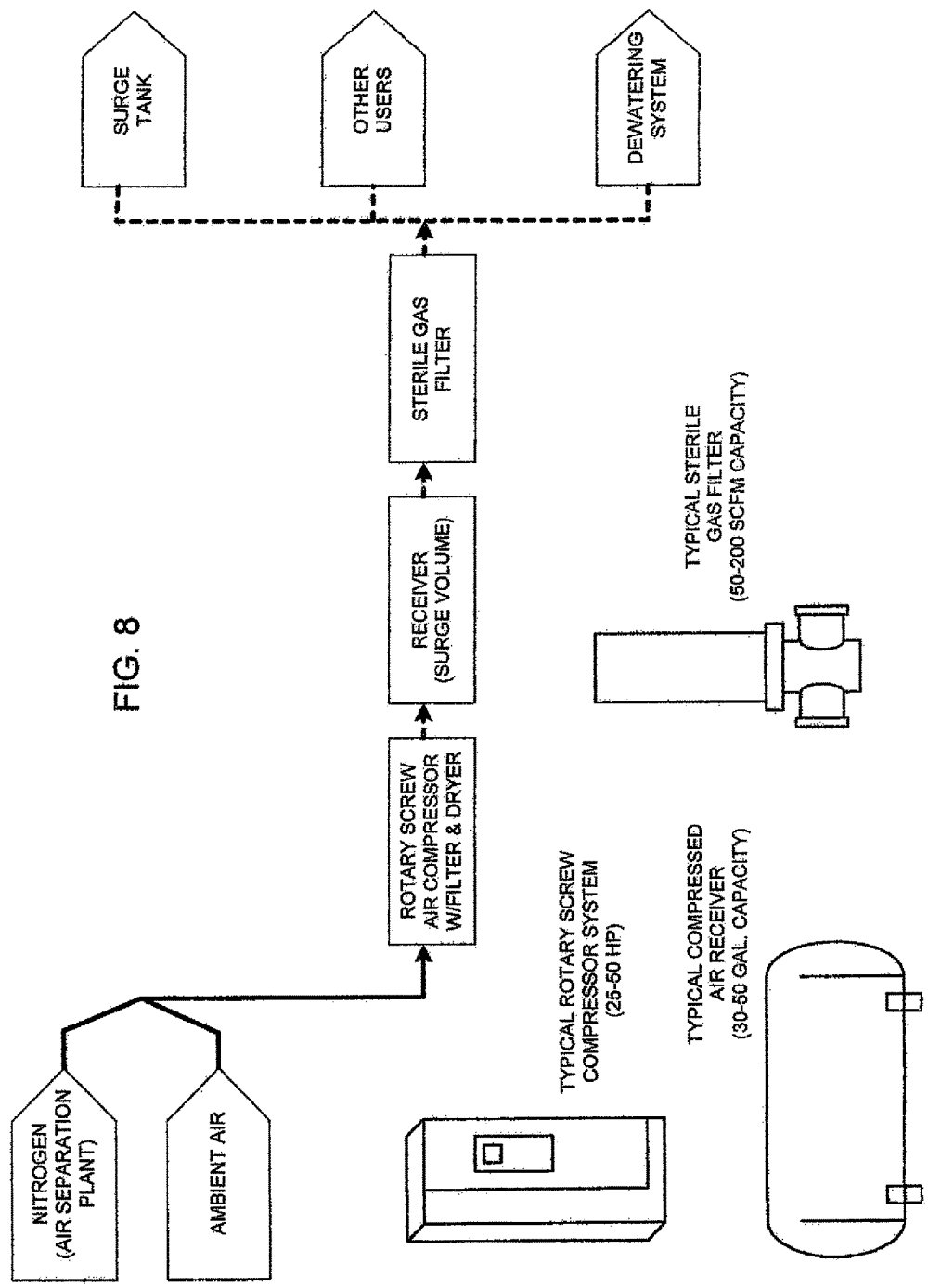

FIG. 8—Sterile Gas System. This system provides the required gas for acting as a protective blanket keeping intruders out of the system. Because the incoming gas is essentially dry it can provide the cooling necessary to keep the media within ideal temperature operating ranges. This cooling is done by evaporating a small portion of the media water and the evaporated water "carries" the surplus heat from the system and is rejected to the environmental atmosphere. This sterile gas can be surplus nitrogen from an operating air separation facility or simple ambient air which must be dried, compressed and sterile filtered prior to use. Both systems are shown in schematic form.

Figure 9:
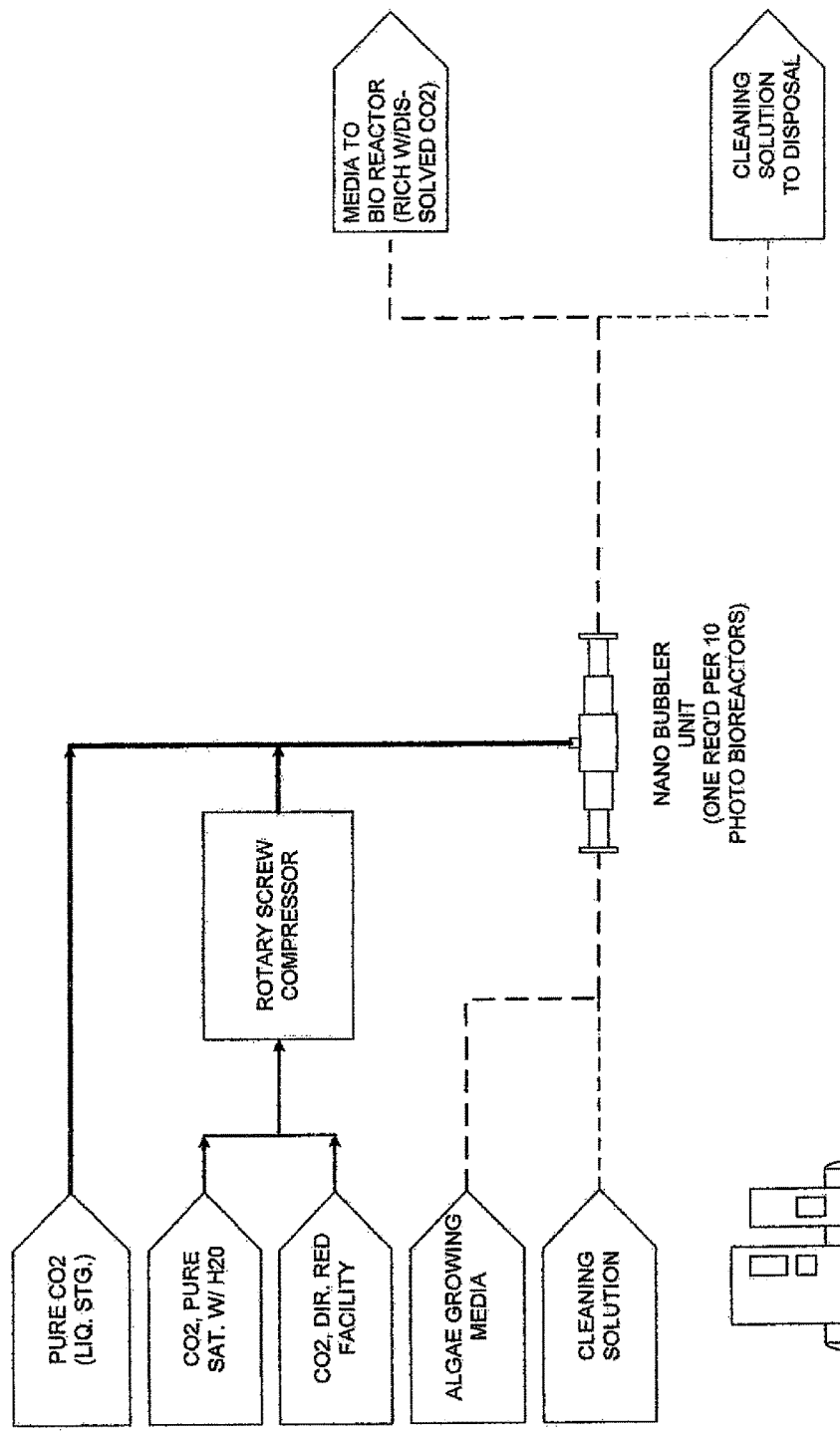

FIG. 9—Gaseous Carbon Dioxide ($CO_2$) System. This system displays the normal feed stock for a photosynthetic microalgae growing system. The carbon dioxide can be from "bottled" or previously extracted and refined or waste CO2 which can be found in any number of industrial processes which are presently vented to the atmosphere. The invention process can utilize any number of gases as long as the volume or mole % carbon dioxide is at least 20% and no heavy metals, which will contaminate the product algae, are contained. Typical industrial waste gases containing carbon dioxide are released to the atmosphere and these must be compressed to 2-3 atmospheres of pressure. This process often brings corrosion issues which have been solved previously by operating a standard air compressor in a mode which does not allow the compressed gas to condense any water that may exist with the incoming gas.

Figure 10:
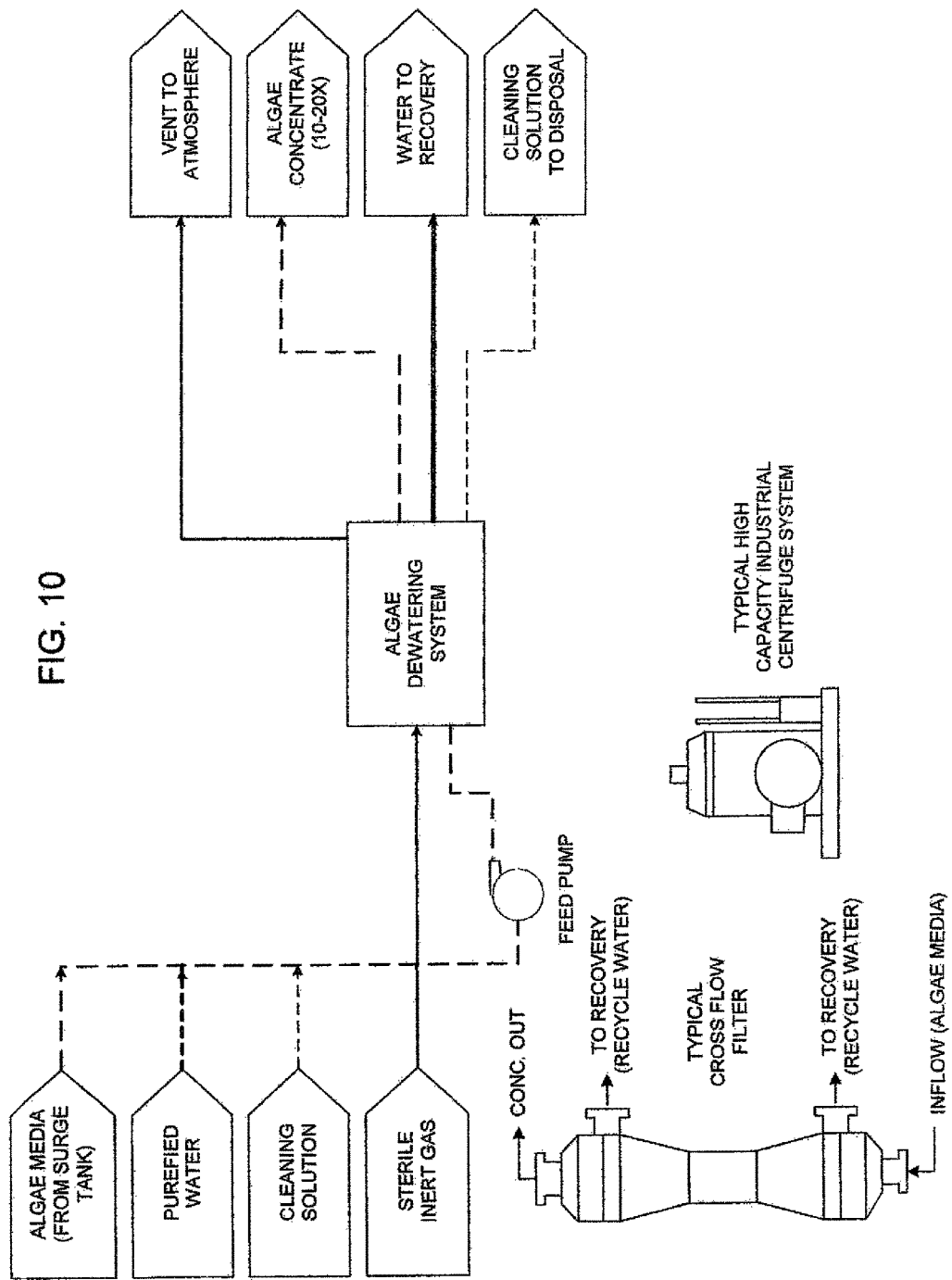

FIG. 10—Dewatering System. This system concentrates the grown algae to a level specified by the ultimate customer depending on final product use. Currently the system uses either cross flow filtration, developed for the pharmaceutical industry, or a modified centrifugation process. Both these candidates are available from several commercial sources and the actual system will be specified for each individual customer.

Figure 11:
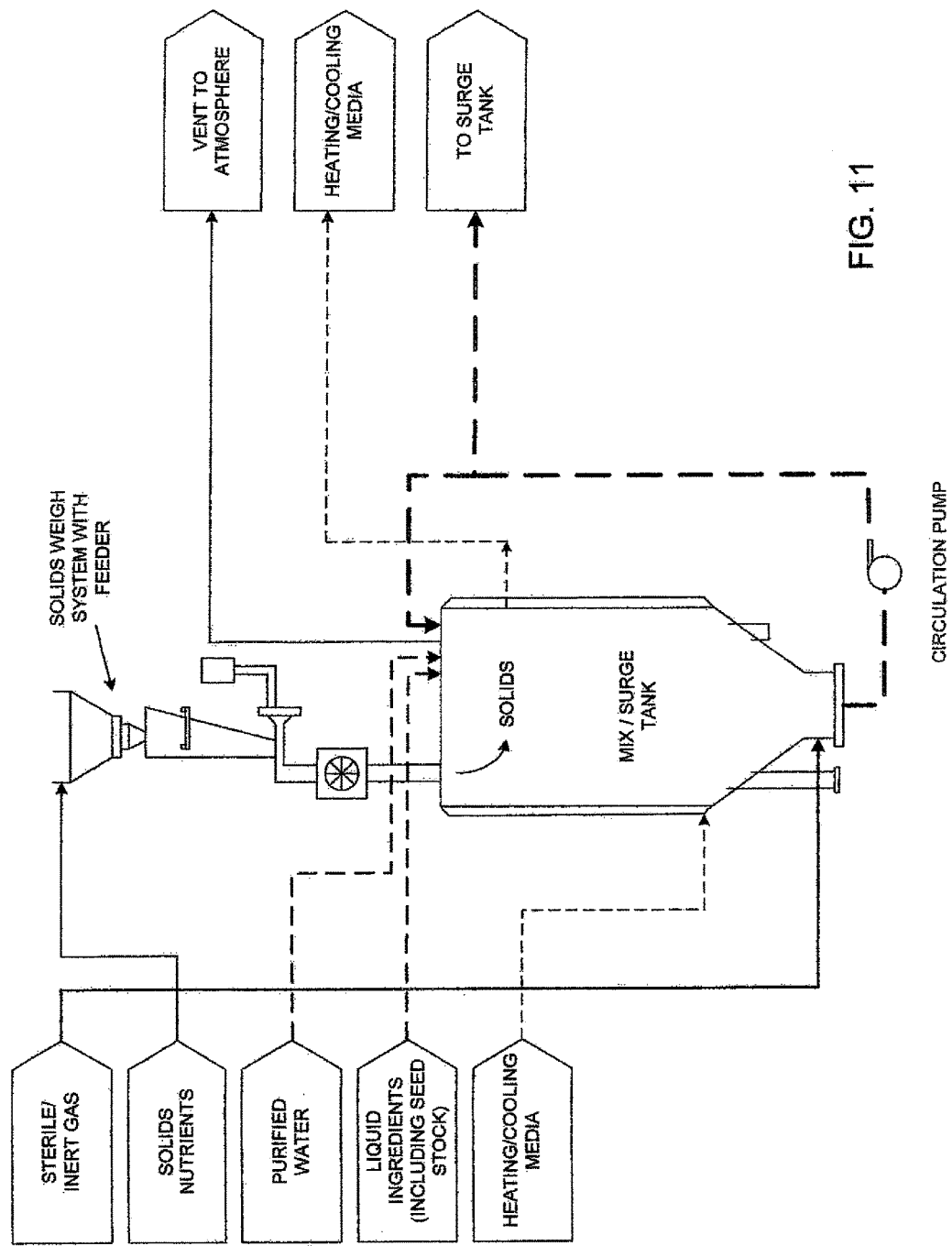

FIG. 11—Seed Stock and Nutrient Introduction System. This system consists of a mixing or blend tank and introduction pump. The materials are first fabricated to the desired concentration and then introduced to the surge tank in the invention system. The high turbulence of the system ensures that the material is almost immediately blended and available to the entire growing media volume.

Figure 12:
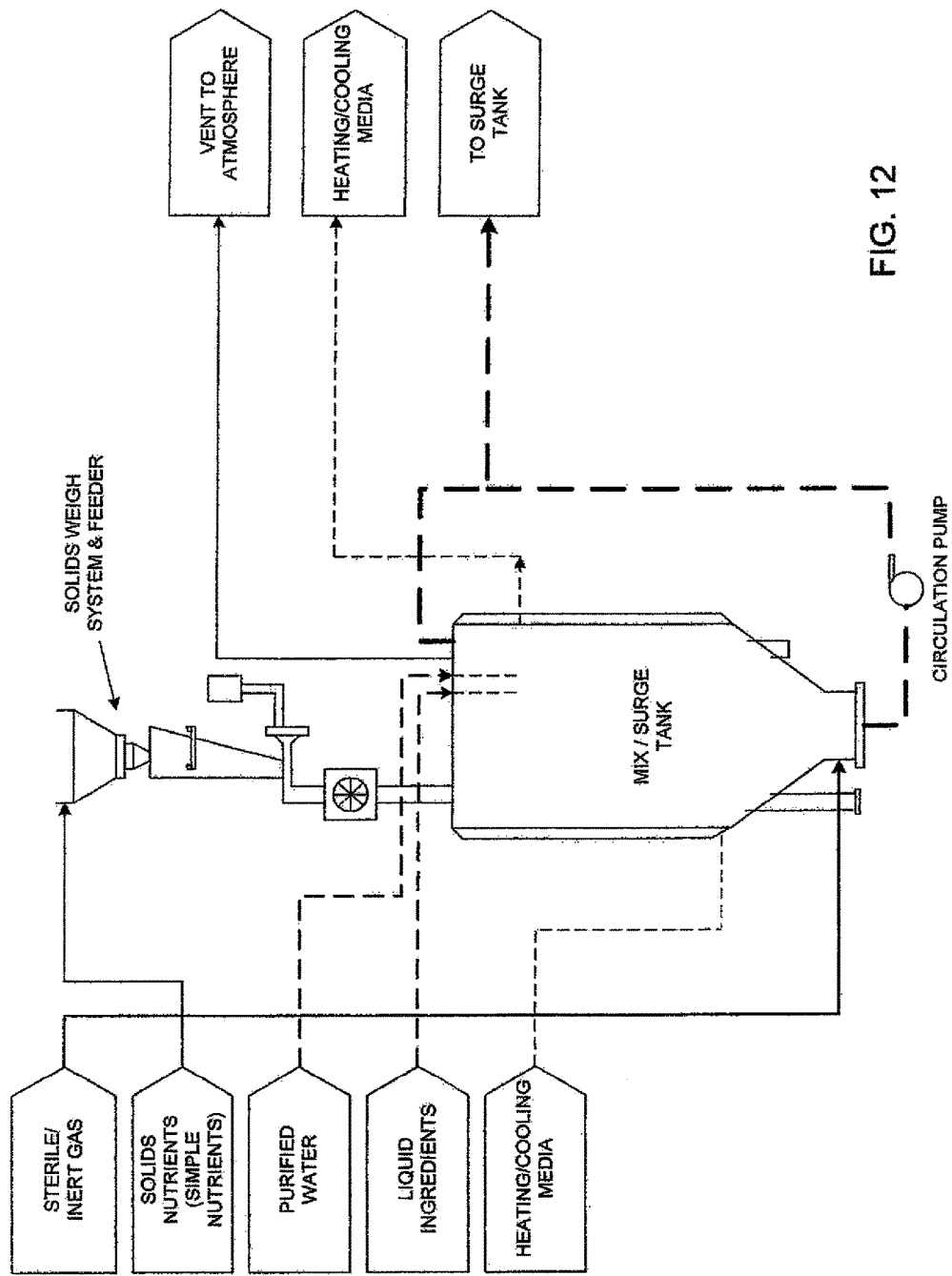

FIG. 12—Modifications/Additions Required for True Mixotrophic Growth. This schematic shows the required addition. It consists of a mix tank which blends the simple carbohydrate and a pump which introduces it to the actual algae growing system. This allows 24/7 growth and enables various current waste streams to be converted into useable microalgae biomass.

Figure 13:
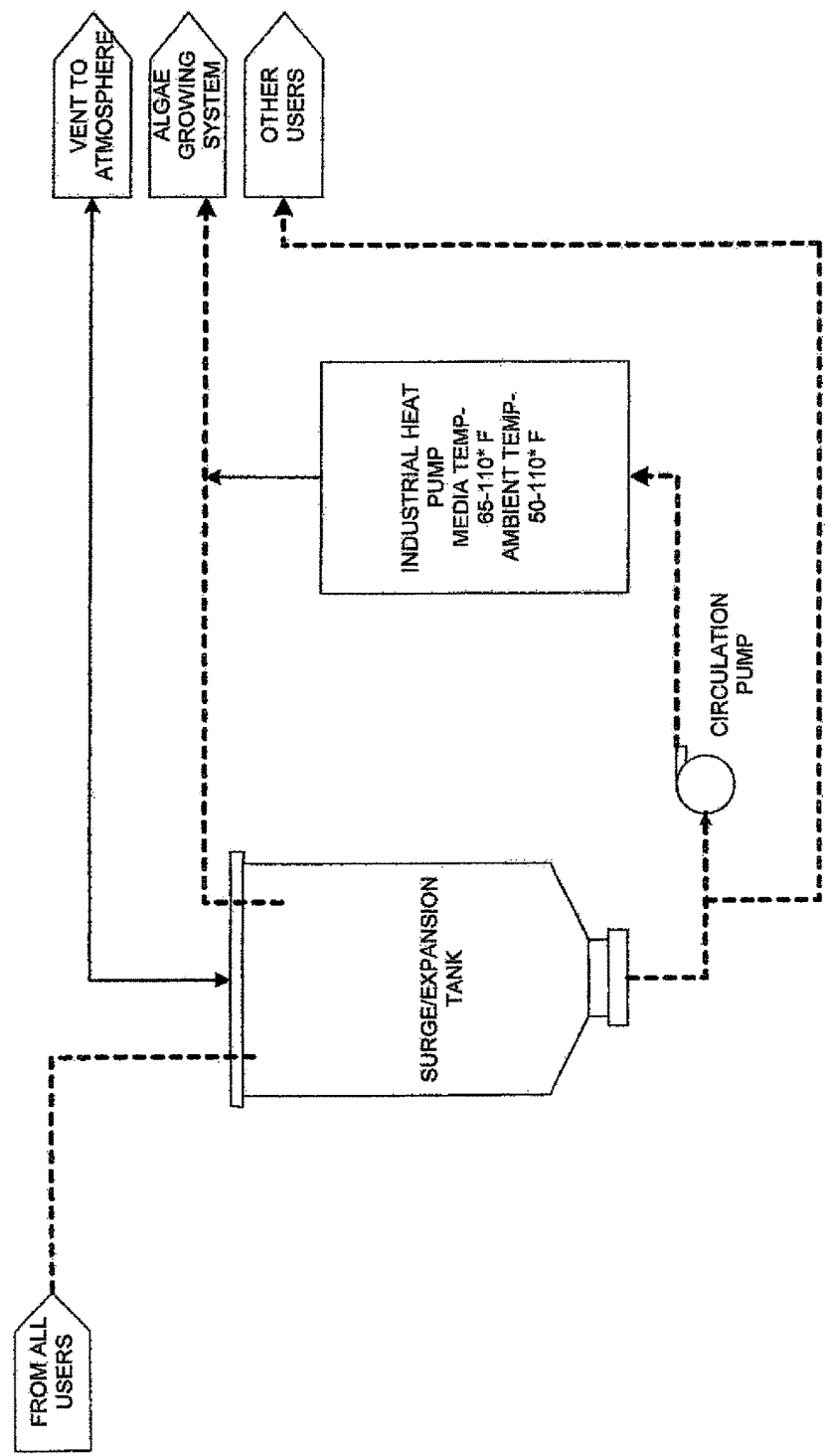

FIG. 13—Media Heating/Cooling System. This schematic shows a typical system that would allow media heating/cooling during non-optimal times. The plan is to use a mixture of propylene glycol and water as the actual heat transfer medium and an external heat source. The source could be an industrial size heat pump because of the relative low temperature extremes required. The propylene glycol was selected because of its physical characteristics, i.e. miscibility with water, boiling point, freeze point etc. and more importantly because of its overall low toxicity to living things. This material is often used as diluents in contact medications for humans.

The same reference numerals refer to the same parts throughout the various Figures.

DETAILED DESCRIPTION OF THE INVENTION

Open microalgae growing systems currently being used for commercial production of algal biomass and bioproducts largely mimic ponds and drainage ditches.

Open raceway technology circulates growth medium around an oval track that is often powered by a paddlewheel that serves to drive the medium around the oval raceway, mix the culture and aerate the growth medium. Good examples of commercial systems based on raceway algal culture are the production systems of Cyanotech (Kona, Hi., USA) and Seambiotic Ltd. (Ashkelon, Israel).

Enclosed microalgae growing systems currently at commercial or pilot-scale are largely of two types—glass tubes (such as the astaxanthin systems used by Algatechnologies, Ltd. located in Eilot, Israel) and plastic disposable hanging tubes (such as used by Algenol, Inc. located in Ft. Meyers, Fla., USA). Both approaches depend on the presence of the needed nutrients, seed stock and carbon sources. These components will be processed by the microalgae and form the biomass which will accumulate until competitive forces or a nutritional limitation impede maximal microalgal growth. This competition could be from other non-target microalgal strains or various competitors and predators that find the microalgae a suitable diet (such as protozoans and crustaceans). Or the competition can be their own cells as they become denser and shade each other they compete for the sun's energy (self-shading). These factors are seen today in the microalgae growing industry with predictable results as outlined above.

The current invention, the Pure Algae Growth System (PAGS), seeks to overcome existing constraints by utilizing proven industrial unit operations that guarantee an environment that offers control of the species of microalgae being grown, reduces contamination by competitors and predator species, and optimizes the environment for algal cultivation. Additionally, most current microalgae growing systems operate in a batch mode with significant time required for startup, cleaning and etc. All these conditions are non-productive and this is reflected in the cost of algal biomass produced. The current invention has several novel features which minimize these penalties. These features include: easy scale up within an enclosed loop, pressurized reactors, continuous operation, and in situ cleaning whenever required.

The present invention is an innovative microalgal culturing system comprising a pressurized mixing and recycling chamber, pressurized modular light reactors enclosed in transparent or translucent materials, and a liquid pumping system capable of circulating the algal cultures in turbulent flow greater than a Reynold's Number of 10,000. The pressurized mixing chamber is used to assure that introduced inputs (e.g., macro- and micronutrients, fresh medium, and makeup water) are efficiently and homogeneously distributed throughout the entire system. Additionally, the mixing and recycling chamber allows efficient introduction of carbon dioxide ($CO_2$) and removal of excess oxygen ($O_2$). The pressurized mixing and recycling tank provides the pressure needed to drive the algal culture into the modular light reactors and through the entire loop for return to the mixing tank. The applied pressure expands the modular reactors and ensures that any transfer of materials or gases is out of the culture system, thereby reducing the chance for contamination.

Figure 1:
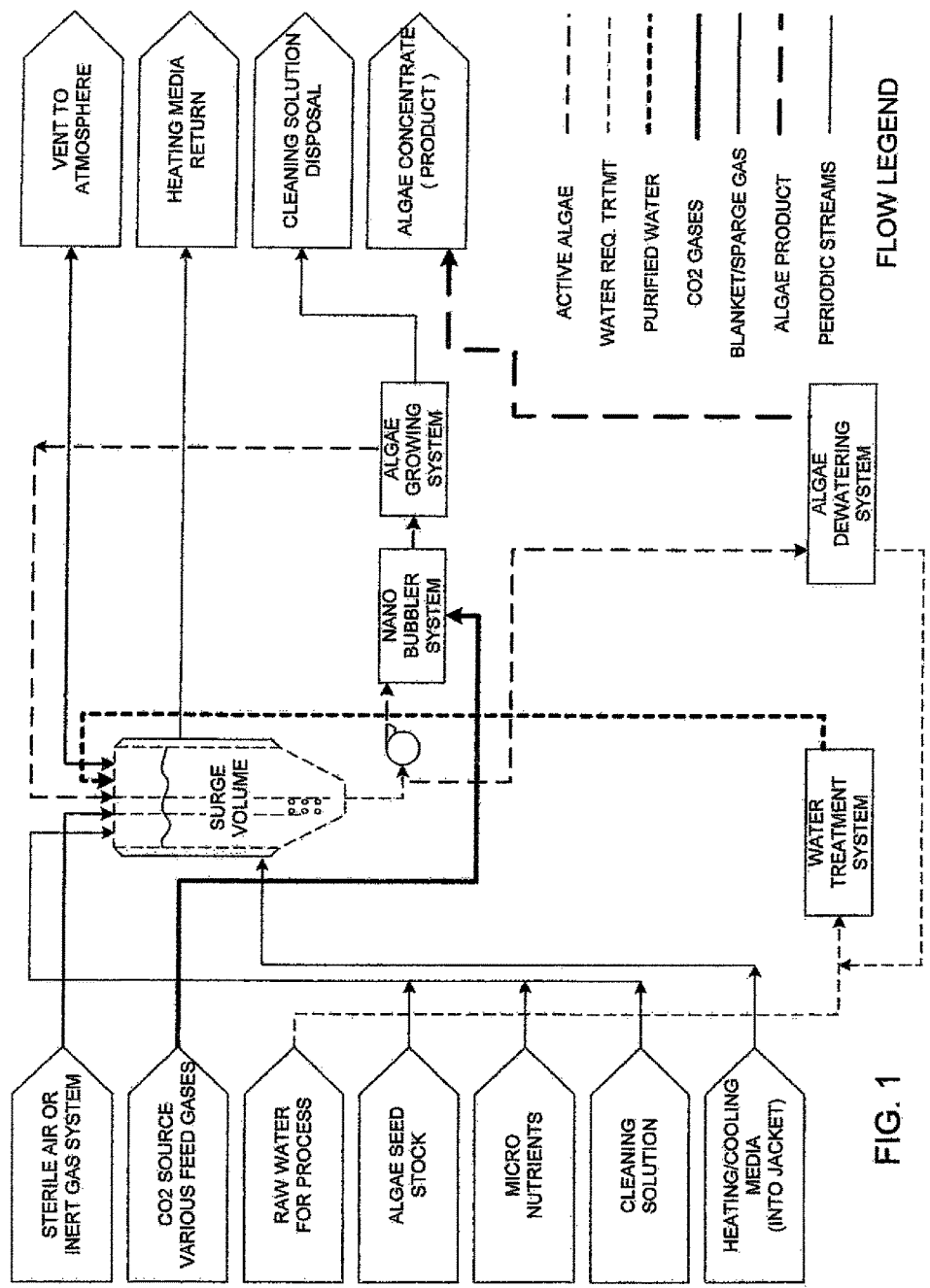
FIG. 1—Process Schematic. This displays an overall schematic of one possible configuration of the Pure Algae Growth Systems process and its component systems of the instant invention. This configuration consists of material inflows which can be characterized as: 1) a sterile, inert gas which acts as both a "blanket" which blocks intruding species as invaders and provides media cooling when necessary by a novel in situ evaporation process; 2) a feed gas which contains CO2 (carbon dioxide) which can be pure or a by-product of several industrial processes; 3) water which can be of considerable impurity as all of it must be treated to a high level prior to coming into contact with the micro algae; 4) algae feed stock which actually inoculates the growing process; 5) various micronutrients which all growing things require to grow and multiply. This stream could also consist of simple sugars which can be used to grow micro algae during non daylight hours; 6) cleaning solution which must be used when the micro algae species growing is to be changed; 7) heating/cooling media which sometimes could be required if growing conditions (temperature) are less than ideal. This material does not contact the actual algae itself but is present, when needed, in the surge volume or tank "jacket".

The process schematics of one Pure Algae Growth System of the present invention design, as shown in FIG. 1, define an pure algae growth system applicable to many varied end uses. Modifications of the present invention will be made as needed to ensure that: 1) the end use of the microalgae is taken into account, e.g., human food applications will need to match regulatory requirements; 2) requirements of the cultured species are met, e.g., specific growing conditions such as nutrients and light; and 3) the type of dewatering required, e.g., filamentous versus single celled algae. Additional modifications will be required to accommodate different raw materials such as use of non-potable water, waste waters, addition of fixed carbon substrates, or use of industrial carbon dioxide emissions. All these process equipment additions or modifications are physically known and used in other processes and can be added to the present invention with no or minimal operational risk.

Modular Light Reactors. System Startup—Scaled up current microalgae growing operations proceed in a batch wise fashion. By necessity these cultures must start at a test tube level and proceed to perhaps a million liters of active culture. Typically, cultures of increasing scale are grown outside and therefore each successive batch "growth" must be less than 100 times the parent's volume. This allows the wanted culture a numerical advantage over the "wild" strains that are always present.

These factors force a typical scale up, from test tube to a million liters, to require several weeks with associated loss of system production and increased susceptibility to culture crashes and non-productive contaminated media disposal. The current invention is designed to minimize or eliminate these hazards by its construction, operation and contamination safeguards. The modular light reactors can be made with flexible or rigid translucent or transparent materials that allow optimal light penetration for maximal photosynthesis.

Additionally, these reactors are designed to be brought into the production cycle sequentially when the culture density has reached an optimized level. This sequential introduction of additional light reactor modules, facilitated automatically through the mixing and recycling chamber (essentially a manifold), removes the need for serial transfers to larger and larger culture volumes (with associated pumping and chance of contamination) as most often applied in current raceway systems and enclosed photobioreactors. The PAGS system is also designed to deliver turbulent flow in the modular light reactors that provides significant advantages to the algal production process. This turbulent flow circulates the algae at flow rates greater than a Reynold's Number of 10,000. This flow minimizes the amount of time that the algae spend in the interior of the culture, where light levels are limiting. It also provides a scouring effect on the inner walls of the modular light reactors to minimize the accumulation of biofilms (which reduce light and are sites of bacterial amplification). The turbulent flow also maximizes the mixing of gas bubbles containing the $CO_2$ to keep the gas and algal cells in better contact, thereby maximizing the available $CO_2$ for cellular growth.

The above features allow the use of simple sugars to act as food when sunlight is not available. The quick response of the PAGS process will allow residual $CO_2$ to be stripped from the medium in approximately 4 minutes and simple sugars introduced as replacement food. This is a unique feature of PAGS which permits operation in a true mixotrophic mode. Typically, the use of fixed carbon growth process (heterotrophic growth) is much faster than the phototropic process allowing more than doubling of the biomass yield on a daily basis.

Materials of Construction—Current microalgae growing systems employ materials of construction that are normally disposed of after use. This invention uses robust materials to build the modular light reactors that are tolerant to sunlight, nearly identical to water in light transmission and can be repaired in place. This robustness translates to less lost production time and a lower unit cost for the algae.

Careful selection of the plastic to be used in the modular light reactors is required to provide maximal light transmission in the PAR region, withstand continuous assault from UV in sunlight, withstand the pressure supplied internally by the system and be simple to work with. A description of the parameters being met by the materials used to make the modular light reactors is provided in FIG. 4.

Growing algae in flexible polymeric tubes requires major compromises. A large volume, hence big diameter, would seem to increase the potential growth rate. However, increases in growth are limited by the amount of sunlight that is available and for high density cultures only a small "rim" nearest the sunlight is actively growing.

Even with extreme turbulence, a diameter representing the best economic tradeoffs (capital cost, performance and robustness) is required. Past experimental work in Hawaii indicates that an outside diameter of about 100 mm represents the best solution for low latitude outside culturing. The diameter is small enough to allow known plastics to provide the required tensile strength and existing polymer extruders can produce tubes of sufficient wall thickness and quality to allow use.

Fully developed turbulent flow within the tube requires the use of materials with a tolerance of the required pressures. The tube will fail in hoop stress, which can be represented by the equation: tau (shear tensile force)=Pressure (PSIG)×Diameter (length)/Wall Thickness (length).

Using our selected tube diameter of 100 mm about 10 cm (4 inches) and a reasonable wall thickness [about 1 mm (0.040 inches)] and an internal pressure 20 PSIG yields a required tensile strength of $13.6 \times 10^6$ Pa (2,000 lb/in$^2$). This is a required working tensile strength and a safety factor of 2-3 must be included to allow for imperfections in the polymer and the extrusion process itself.

Olefins fail this required tensile capability and are therefore not useful for this invention. It is common to extrude polyethylenes (both high and low density) and polypropylene. These materials are relatively inexpensive and are true plastics. Plastic is derived from the ancient Greek word, plastikos, which roughly translates to formable. The olefins have no true elastic range; this is when stressed by internal pressure actually returns to its original shape and dimensions. They immediately begin to yield and the diameter increases. This causes the wall to become thinner, as the diameter increases, and catastrophic failure occurs almost immediately. The obvious answer is to increase the wall thickness of the tube. However, this degrades light transmission and makes the tube heavier and more expensive. Also the extrusion process becomes more difficult and a final wall thickness of about 0.040" is about the practical limit for most known plastics.

Suitable tensile strength polymers could include nylons, super strength ultra-high molecular weight polyethylene and a class of compounds known as polyurethanes. Also the positive pressure of the system ensures that it will "leak out"; if minor failures occur preventing intrusion and subsequent contamination during repair operations. Nylons do not transmit light well and the ultra-high molecular weight polyethylene has not been successfully extruded as yet (their use is presently limited to high value items such as armor plate and bullet proof vests) for personal protection.

Polyurethane is formed by reacting an isocyanate with various chain length polyols (contain multiple OH groups). It is known how to tailor the desired flexibility and tensile strength and apply using extrusion technology has been around for years. Polyurethane tensile strength (typically shown as ultimate) is listed at about 10,000 lbs/in$^2$ which would allow a safety factor of about 4-5 for this application. Ultraviolet light resistance is high for these compounds and exposure to full Hawaii sun for 4-5 months was found to only cause slight yellowing and no apparent degradation of tensile capability.

The strain expected on the materials in the wall of the modular light reactors is graphed in FIG. 5. Since the predicted requirement for tensile strength is 2000 lbs./square inch, it is obvious from FIG. 5 that LDPE and HDPE are not appropriate for use in the PAGS system. The current materials used in the PAGS pilot system are a proprietary polyurethane produced by Nu-Methods (Cuyahoga Falls, Ohio, USA). It is a seamless tubing, custom formulated using a polyurethane blend with a proprietary UV resistance package and does not contain phthalates. The resin can be extruded as tubing, blown film and heavier wall (1 mm) sheet/roll goods as needed. It is FDA-acceptable and EU food safe for direct food contact and packaging. It was tested for high light stability using an 800 hour heli-arc light exposure test (FIG. 6). This polyurethane shows very minimal to almost no darkening and should remain viable for over a year in the modular light reactor.

Culture Density—Current commercial microalgae growing systems have little overall agitation or must spend significant additional energy (cost) to accomplish this. The mixing is required because only a very small region of the actual existing system has the right mix of photons, nutrients and other necessary materials.

Also in existing commercial systems significant temperature variations in the medium adversely affect overall growth rates. The invention uses fully turbulent flow in the modular light reactors, which greatly improves the overall system growth rate and allows higher culture density. This higher density requires a much less expensive dewatering step later on when the microalgae are actually converted to a commercial product.

Growing Environment—Current microalgae systems are largely grown outside and are exposed to natural contamination from wind or other surface borne contamination sources.

The invention grows the microalgae in a controlled environment that is free of contamination sources by design. This factor in conjunction with the proven initial feed stock guarantees a healthy culture which can multiply at an accelerated rate. The invention also allows food and nutrients to be introduced at a predictable rate which insures optimum growth rate.

Mixing and Recycling Chamber/Temperature Control—The mixing and recycle chamber (surge tank) has several uses and is the process control center of the PAGS system. These uses include:
1. Removal of the oxygen generated during the previous cycle or passage through the growing tubes. Forced removal of the product oxygen encourages the desired reaction to proceed more quickly than competing systems.
2. Cooling of the media which may adversely affect the photosynthesis process; if temperatures above 35° C. are reached. This cooling is done in the same process as the oxygen removal and can be adjusted to maintain optimal growing temperatures by adjusting the flow rate of the dry gases that are being introduced into the surge tank.
3. Heating of the media if the temperatures of 20° C. or lower are reached during cold periods or via night time cooling. This improves system or growth rate startup as all reaction rates will increase with higher reaction temperatures.
4. Introduction of required micronutrients or vitamins that may be needed for optimum growth rates.
5. Acting as a central control volume where process variables are measured and appropriate actions are initiated. The quick response time for the entire system maintains optimal growth conditions.
6. Provides a surge volume suitable for multiple photobioreactor modules. The single point of control for all growing modules encourages optimal growth conditions and significant capital cost savings.

These specific functions are described briefly below.
1. Oxygen Removal—The oxygen formed during the photosynthesis process is removed via stripping by sparging with small bubbles of elemental nitrogen. This process is used industrially and specific ratios are known for oxygen removal. This encourages our desired photosynthesis reaction and will improve drastically the overall biomass growth rate.
2. Media Cooling—The temperature of media will increase during the photosynthesis process. This increase is largely due to infrared heating from the sunlight. The cooling process will occur because the bone dry nitrogen which is used for positive pressure maintenance in the system will actually vaporize some water and carry it out of the system. Water has a latent heat capacity of about $2.2 \times 10^6$ J kg$^{-1}$ (1,000 BTUs per pound) and the bone dry nitrogen will exit with about 5 mole percent water at the expected temperatures. The flow rates of the nitrogen can be adjusted to maintain optimal media temperature for growth. This is done by sparging nitrogen (which is bone dry) contained in very small bubbles. The nitrogen has very low solubility at this pressure and in addition to stripping the product oxygen it will evaporate water as well. The latent heat of water is high (about 1,000 BTUs/lb.) and this evaporation will cool the media to a desired growing temperature. The nitrogen acts as an in situ cooling tower. Commercially nitrogen produced by a cryogenic separation process from air is often a surplus product that can be obtained at little capital cost. The separation process ensures that it is both sterile and bone dry; both features needed for this application.
3. Media Heating—The temperature of the medium could drop below the optimal growing range. This could be caused by night time cooling via radiation or actual cold air temperatures. Temperature adjustment will be done using a mixture of polypropylene glycol and water in the jacket of the surge tank. Polypropylene glycol is much less toxic to living things and is often used as diluents in pharmaceutical preparations.
4. Required Micronutrient Addition—These items will be consumed during photosynthesis process and can be added directly to the system via the surge tank.
5. Central Process Control—The PAGS system will have very short response times. This is because the medium is circulated very rapidly and the process variables will essentially be real time for very nearly the entire system. This is very different than a large open pond where actual circulation may be measured in hours. This feature will allow the entire system to be maintained at optimal growing conditions regarding process variables and reactant concentrations.
6. Required Surge Volume—Each photobioreactor module pump will transfer medium in the hundreds of liters per minute flow rates. Additional modules will require the availability of a significant "heel" in the tank to insure that all pumps will not be starved or cause cavitation. The surge tank is designed and specified such that up to 10 modules can be served by one tank. This feature will allow significant economies of scale and capital cost reductions which do not exist in the conventional open pond set up.
7. Carbon Dioxide Utilization—The PAGS process uses pressurized carbon dioxide in a contained space. This results in as much as a 20-fold improvement in carbon dioxide utilization over existing commercial systems. The technique was first used at a commercial installation in Hawaii where the carbon dioxide was a waste stream from an industrial process (a naphtha reformer). This installation was developed based on an EPA grant award for novel sourcing of microalgae feedstock. This initial concept has been improved by locating superior materials of construction for the actual microalgae growing volumes. This capability affords a much broader choice of waste gases for the microalgae food. Volume or mole percentages as low as 25% carbon dioxide will provide adequate food stock with minimal degradation in carbon dioxide utilization.

The modifications required for the PAGS process to utilize this lower quality food are merely slight increases in the gas handling systems.

Current microalgae systems use carbon dioxide (which must be dissolved in the growth medium) or a simple carbohydrate as food for promoting the algae growth. Existing algae growth systems are open to the atmosphere and normally very shallow making introduction of $CO_2$ difficult and reducing off-gassing also difficult. Feed materials, such as gaseous carbon dioxide, are introduced with little opportunity to be incorporated in the algae growth medium and most $CO_2$ is simply vented (lost) to the atmosphere. The PAGS system is closed and under as much as 2 bar of pressure. This greatly increases the solubility of the carbon dioxide, which permits the algae to more efficiently take it up and channel it to enhanced growth.

The carbon dioxide could be naturally occurring or introduced as a mixture of gases. In either case the utilization of the carbon containing food is quite low. If introduced as a gas previous geometries of the algae growing systems almost insured that most of it was wasted and vented. The current invention uses a higher partial pressure of the carbon dioxide to enhance the dissolving process. The result is high food utilization and its attendant reduced component cost. Currently, the PAGS system uses high concentration $CO_2$ to charge the system and flushes out excessive oxygen with nitrogen or inert gases When any gas is in contact with water, some gas will dissolve in the water. The amount that will dissolve in the water depends on the pressure (or partial pressure if the gas is a mixture) and temperature. Gas solubility (the amount that can be dissolved) is inversely proportional to the temperature.

Henry's law quantifies this relationship and has been used to design and characterize functioning industrial processes where mass transfer from a gas to a liquid is an inherent part. A table of measured Henry's Law constants is shown below for some common gases at a temperature of 25° C. (Table 1).

TABLE 1

| Values of various gases at 20° C. | |
|---|---|
| Gas | K(h) (atm/mole) |
| Oxygen ($O_2$) | 769.23 |
| Hydrogen ($H_2$) | 1282.05 |
| Carbon Dioxide ($CO_2$) | 29.41 |
| Nitrogen ($N_2$) | 1639.34 |
| Helium (He) | 2702.7 |
| Neon (Ne) | 222.22 |
| Argon (Ar) | 714.28 |
| Carbon Monoxide (CO) | 1052.63 |

Using these constants, what is the concentration of $N_2$ in water (with a pure $N_2$ atmosphere)?

$$K(h \text{ for } N_2)=1639.34=P(N_2)/(N_2 \text{ aqueous})=1 \text{ atmosphere}/X$$

$$X=6.1 \times 10^{-4}=0.00061 \text{ moles/volume}$$

Since air is 78% $N_2$ (by volume or moles)

$$X'=0.00061 \times 0.78=0.00048 \text{ moles/volume}$$

$CO_2$ is much more soluble than nitrogen and for a pure $CO_2$ atmosphere $$K(h \text{ for } CO_2)=29.4=Pco2/(CO_2 \text{ aqueous})=1 \text{ atmosphere}/X$$

$$X=0.034 \text{ Moles/Volume almost 100 times the concentration of nitrogen}$$

In the PAGS system the pressure at the $CO_2$ introduction is approximately 2 atmospheres (of pure CO2) and therefore the equilibrium value is nearly 0.068 Moles/volume. We will be introducing only a small fraction of that amount (roughly what the algae can consume during their "visit" to the photon source) and the nanobubbler device will ensure visible bubbles will rarely if ever be seen.

Oxygen is generated during the photosynthesis process. The photosynthesis reaction (as are all reactions) is reversible and the presence of oxygen will slow the overall desired reaction. The product oxygen will be largely removed from the media by stripping with gaseous nitrogen in the surge tank. This technique is commonly used in industry and very low residual oxygen concentrations can be attained. Some unreacted $CO_2$ will also be stripped but its superior solubility (26 times that of oxygen) will minimize this loss.

The projected utilization of $CO_2$ is perhaps 20 times better than existing systems. The actual growth rate of biomass will also be significantly better than existing systems. This is because of the optimal growing conditions in the PAGS process:

High pressure and equilibrium solubility for the dissolving process
Preferential removal of oxygen for the reverse reaction.

As new technologies are produced to separate gases economically, recovery and recycling of the $CO_2$ when the oxygen is purged could improve the carbon balance of this system. Unfortunately, current technologies are not available for this process.

This same recycle feature is possible with the micronutrients and macronutrients that are not consumed and remain in the spent algae growing medium. These compounds are simply carried along with the water on dewatering and can then be recycled for further growth. Component utilization efficiencies with the PAGS system are perhaps 10 times existing systems.

Any gas introduced to stimulate algae growth must first be dissolved in the algae growing media. Existing systems have a simple "sparge" device which produces large bubbles of gas. These bubbles have significant buoyant forces and simply rise quickly to the surface and are vented and lost. The PAGS system uses unique nanobubblers which produce very small bubbles. These bubbles have very high surface area to volume ratios which yield very productive mass transfer rates (and associated high material utilization and efficiencies).

The PAGS design maintains carbon dioxide in solution phase over the entire length of each modular leg through a novel introduction and retention system. The $CO_2$ is introduced as a nanobubble in the mixing and recycling chamber under pressure higher than atmospheric. The $CO_2$ loaded culture is passed into the modular light reactor and turbulently mixed throughout its entire passage, thereby ensuring any $CO_2$ off-gassing is prevented.

System Cleaning—The PAGS process is designed to be cleaned in place. These processes are used routinely in the pharmaceutical and food industries where contamination can grow and make their product unsuitable for sale. This feature was integrated into the basic design by selecting the process equipment and interface connections for the items actually contacting the microalgae growing media. Special chemicals have been selected which perform these cleaning functions in the above mentioned industries. This feature will allow quick turnaround and little or nor component disassembly when microalgae species growth must be altered by operators of the PAGS process.

Biofloc/fouling control. The turbulent flow of the light reactor chamber has the added advantage of preventing the formation of biofilms and biofloc within the modular light reactors. This reduces the labor required to clean the system, prevents attenuation of the light passing into the light reactors (due to shading by adherent biomass), and lowers the risk of colonization of the adherent biomass with bacterial contaminants. An alternative approach can be used to deal with very sticky algal cultures. Due to the strong turbulent flow of the system the inclusion of plastic beads in the medium will provide additional physical mechanism to increase the self-cleaning capacity of the system. The beads are actually spherical bodies made of plastic about the same specific gravity of water. The turbulence will "bounce" these "balls" along the tubular walls thereby keeping them clean and enhance the passage of the required light Latitude Applicability—Current microalgae growing systems use natural sunlight and warmth to grow the algae, therefore, they are competitive largely in the tropics and subtropics where light and heat are readily available.

There are many candidate applications where the winters are extreme and microalgae cannot be grown outside during that period. Such opportunities could be abundant raw material availability or physical needs where an algae product should be grown in cold regions. The PAGS system can be easily grown indoors with synthetic and/or selected wave length light sources. Current light emitting diode (LED) technology allows a specific wave length of light to be generated via a very efficient energy conversion process. Commercial sources of these LED devices are readily available. The invention allows indoor growth and temperature regulation such that no location is off limits.

Selective Species Growth—Nature grows a "family" of living things in a specific environment. This affords natural protection from predators and insures survival of the species by allowing the strongest to survive. When we grow crops with only one plant or animal present we offer a virtual feeding ground for specific predators. The PAGS algae growing system offers a "closed environment" where outside influences are virtually nonexistent. Materials such as food, diluents, or carrier media are carefully screened and cleaned to an almost totally sterile condition. This brings an Eden like growth condition for specific algae species. Conditions such as food concentration, temperature and chemical conditions (acid or base condition) are all optimized for the intended growth of a specific species.

Operation Function—During routine operation the media flows through the actual polymeric photobioreactors. The flow rates are high enough to prevent the algae from adhering to the photobioreactor wall; thereby blocking the required light admission. This feature is similar to the design of sewers where a "scour velocity" is designed in to prevent sand or other solids deposition interfering with the water flow. This high velocity media is permitted because of the tensile strength of the polymeric material and its minimization of U-turns which represent almost all the required pressure loss to maintain high flow rates.

The actual latitude (climate conditions) for the installation. Installations far removed from the equator may require artificial light sources of specific wave lengths for optimal growing conditions. The subsystems described in the aforementioned schematics are composed of commercially available components widely used in industrial applications.

Mixing—Present commercial microalgae growth systems are largely open ponds or raceways that have paddle wheels to stimulate circulation and mixing of the growth media. These raceways are often large and mixing in the actual media is poor. This manifests itself as the actual growing zone is a very thin "layer" near the actual surface. Mixing is very limited which does not allow those microalgae near the bottom to receive the sunlight necessary to prosper and multiply.

PAGS grows microalgae in circular polymeric "tubes" which are in constant circulation. The circulation is done in fully turbulent flow with a Reynold's Number in excess of 10,000. This allows all microalgae present to spend sufficient time in the growing zone to produce improved overall growth rates. Also the system maximizes the time spent in the modular light reactors with minimal time in the surge volumes where nutrients and feed gases are introduced.

The PAGS polymeric tubes were developed in cooperation with a major chemical company and the material offers very good light transmission as well as superior overall resistance to the ultraviolet spectra of sunlight which degrades most polymeric material quickly.

The PAGS polymeric tubes were developed in an exclusive cooperative project with Nu Methods Plastics Inc. The material has superior light transmissivity, tensile strength and high ultraviolet light resistance which make it suitable for outdoor tropic latitude application lasting several years. The material is also resistant to the seldom used chemical cleaning protocol and can be repaired in place if small punctures or other "operational accidents" occur. The material's tensile strength affords a safety factor of >4 for normal operations including ramped up pressure during system cleaning mode.

Turbulence—Turbulence is integral to the novelty of the PAGS design and helps to provide the system with optimal properties beneficial to the production of algal biomass. Carefully controlled turbulence in the optimal zone for algae growth is important because of many factors. Importantly it increases the region within the system that is capable of supporting optimal photosynthesis thereby stimulating growth and reproduction of the algal cells. As the algal culture becomes denser the importance of mixing becomes higher due to the "self-shading" phenomenon.

More elaborate techniques have been used to deliver non-limiting light to algal cultures such as reduction of the light path length to a few centimeters (U.S. Pat. No. 5,104, 803) or introduction of stacked light guides (Jung et al., 2014). However, for most algae exposure to light constantly is not necessary and rapid mixing such that they are exposed as the correct interval will provide optimal photosynthesis. That is, if the cells are exposed directly to maximal insolation they will often be saturated and undergo a process known as photoinhibition—where the cells dissipate excess light energy as heat and, in extreme cases, degrade portions of the photosynthetic apparatus to protect the cells.

When turbulent flow is used, cells are exposed to maximal light intensity for only a short period and then returned to the culture without damage and replaced with other cells. Exposure in this way allows the best use of incoming radiation so that cells absorb and use all the incoming light but photosynthesis is not saturated or damaged by photoinhibition. This process has to be optimized for the algal species being used, as some are able to function optimally with exposure every 5 seconds while others need light exposure every 30 seconds. Tuning the system for the organism is essential to the best yields.

Alternative carbon source—When cells are no longer provided sunlight growth ceases and respiration is the dominant metabolic reaction. This manifests itself as a sudden spike in pH which is detrimental to the algae itself as well as a decrease or pause in biomass accumulation. The PAGS system can prevent this spike via gas/material introduction and can be modified to provide a fixed carbon source (e.g., sugars and sugar alcohols such as sucrose, glucose, or glycerol) to drive mixotrophic algae growth during the dark periods of the day.

Many microalgae growing systems offer potential use in the mixotrophic mode. This means photosynthesis during daylight hours and some simple carbohydrate food source at night. The PAGS process is uniquely suited to this type operational mode because of the high degree of homogeneity and almost instantaneous response time to process condition changes. This would:

Minimize process condition secondary impacts (high pH spike) such as when changing growth modes or feed stocks.

Drastically increase biomass growth because of longer growth periods (no night time shutdown) and higher food conversion rates when using carbohydrates as feedstock.

Allow optimal harvest of the grown microalgae by keeping the algal cell density in the proper range during the entire operational day.

Comparison of PAGS to production of algae in a conventional raceway system—One possible scenario for running the PAGS system is provided as a schematic in FIG. 2 and a same scale system using a conventional raceway production system is diagramed in FIG. 3. The mass flows of each system have been modeled at the same scale and the information is provided as Table 2.

The PAGS set up is designed with 10 light reactor tubes and the raceway system is modeled as 15×7 meters long with 3 meters wide sides of the raceways. Both are scaled to deliver 3,925 grams of biomass per day. From the modeled systems the outputs were modeled and are presented in Tables 2 and 3. Critical differences in the process are seen in both the types of input and output streams as well as the magnitude of those streams. The PAGS system is much more efficient in incorporation of the added carbon dioxide. It uses 5% of the carbon dioxide to produce the same biomass quantities due to the enclosed design and recycle and reuse design of the mixing and recycling chamber as well as the pressurized system and delivery with the nanobubbler. The PAGS system also is much more efficient in conservation of the water supplied using 350 kg per day compared to greater than 10,000 kg/day lost in the raceway system mainly to evaporative loss and dewatering a lower density culture.

TABLE 2

Model of PAGS process for production of 3,925 grams of dry biomass per day output system.

| Stream | Number | kg/day | Stream Type (Gas/Liq) | Aug Temp © | |
|---|---|---|---|---|---|
| Process Water | 1 | 350 | L | 25 | water all |
| CO$_2$ | 2 | 15 | G | 20 | pure CO$_2$ |
| Micro-Nutrients | 3 | 5 | L | 25 | water 98% Nitrogen 1.8% Phosphorus 0.2% |
| Algae Seed Stock | 4 | 0 | L | 25 | None |
| Nitrogen Gas | 5 | 4,000 | G | 20 | All |
| Heat Transfer Liquid | 6 | 110,000 | L | 35 | propylene glycol/water (50/50 v/v) |
| Dewatering Removal | 7 | 72 | L | 28 | |
| Gas vented to atmosphere | 8 | 4,340 | G | 27 | |
| Heat Transfer Liquid | 9 | 110,000 | L | 32 | propylene glycol/water (50/50 v/v) |
| Algae Product | 10 | 20 | L | 25 | water 90% algae 10% |

TABLE 3

Model of raceway process for production of 3,925 grams of dry biomass per day output system (21 raceways included in the model).

| Stream | Number | kg/day | Stream Type (Gas/Liq) | Aug Temp © | |
|---|---|---|---|---|---|
| Process Water | 1 | 8,916 | L | 25 | 100% water |
| Carbon dioxide | 2 | 300 | G | 25 | 100% CO$_2$ |
| Micro-Nutrients | 3 | 120 | L | 25 | 98% water, 1.8% Nitrate, 0.2% Phosphate |
| Algae Seed Stock | 4 | 160 | L | 25 | 99.5% water, 0.5% algae |
| Cleaning Media | 5 | 8,000 | L | 25 | 98% water, 2% salts |
| Evaporative losses | 6 | 1,300 | G | 30 | 100% water |
| Algae dewatering | 7 | 8,000 | L | 32 | 99.5% water, 0.5% algae |
| Cleaning Waste | 8 | 8,000 | L | 30 | 98% water, 2% salts |
| Carbon dioxide lost to atmosphere | 9 | 85 | G | 30 | Air with <1% CO$_2$ |
| O$_2$ Production | 10 | 11 | G | 30 | Air with <1% additional O$_2$ |

MODES FOR CARRYING OUT THE INVENTION AND INDUSTRIAL APPLICABILITY

Using a variety of methods exemplary embodiments of the invention are directed at improving the growth of microalgae. This is particularly applicable to reduction in the loss of water and CO$_2$ from the production system (see Table 2 compared to Table 3 which compare PAGS to a raceway production system).

The PAGS system is uniquely designed for clean production of algal biomass. Therefore, one of the modes of production is to produce a single alga that is not a rapid grower but produces a useful bioproduct. Such an organism could not compete in open pond systems and the unique design of the PAGS system provides a better culture condition than existing photobioreactors. Such high value products could be secondary metabolites, nutritional oils (e.g., docosahexaenoic acid, arachidonic acid, eicosapentaenoic acid, and other long chain polyunsaturated acids), carotenoids (e.g., astaxanthin, beta-carotene, canthaxanthin, and other unique carotenoids), phycobiliproteins (e.g., allophycocyanin, phyocyanin, and phycoerythrin), polysaccharides (fucomannans, glucomannans, and the like) and other high value compounds. Due to the tightly controlled design of PAGS these could be used as food grade materials for high value applications.

The PAGS system could also be used as an enclosed production system for scaled up growth of genetically manipulated microalgae. Transgenic techniques have the capacity to greatly enhance the productivity of photosynthesis in microalgae, however the fear that unintended release of these organisms could endanger the environment hinders their use in most algal production systems. The design of PAGS could allow contained and controlled growth of such organisms under conditions where regulatory approval is possible and safety can be assured.

The PAGS system could also be used to scrub undesirable pollutants from either aqueous waste streams or vapor emissions. Many industrial processes produce wastewaters that are high in materials useful for algal growth (such as nitrogen compounds, phosphates, and other micronutrients) that could be utilized in the PAGS system to effectively scrub these nutrients and produce clean water. Similar approaches have been used with algae and wastewater in the literature (Perez et al., 2015). Likewise, industrial gas sources produce carbon dioxide and nitrogen and phosphorus compounds that can be effectively converted to algal biomass. While the use of industrial waste mostly precludes the use of the biomass for food and feed applications, purified bioproducts can be made for renewable chemical production. Alternatively, this biomass can be used as a biofertilizer for fields or as a feedstock for biofuel production.

Alternative Feed Materials for the Pags Algae Growing Plant

The PAGS process has been designed as a robust, industrial facility. There is considerable tolerance in the feedstocks that can be introduced and converted into algae biomass. Some of the candidate items are shown in Table 4 and FIG. 9. Table 4 offers the amount of Carbon Dioxide that is potentially available from 4 commodity product systems. The amount of $CO_2$ involved in each of these processes is significant and the units displayed are in millions of metric tons per year.

TABLE 4

Industrial processes producing suitable feed gas for the PAGS process.

| Process/Product | $CO_2$ Content of Gas (mole %) | Total Product Output Worldwide (millions of metric tonnes) | $CO_2$/Product | PAGS Production ($10^6$ tonnes/year) |
|---|---|---|---|---|
| Direct Reduced Iron (Midrex Process) | 25 (1) | 100 | 0.8 | 23 |
| Ethanol (US only) | 95 | 50 | 0.9 | 13 |
| Cement | 40 (1) | 3,500 | 0.9 | 900 |
| Aluminum | 70 (2) | 3 | 0.5 | 0.4 |

Note 1
Solids removal required before use
Note 2
CO removal or conversion required before use The PAGS process could utilize each of the candidate gas streams in the concentrations expected from the parent process operation. The expected penalties for using these materials are:

1. Slight loss of utilization in the feedstock carbon dioxide.
2. Slight increase in the size of the nanobubbler that would be used.
3. Slight increase in the amount of vapor off gas that would need to be handled.

Many of these industrial processes use natural gas as the starting or required component feedstock. Many of these also are located in arid regions where water is either expensive or in very short supply. The PAGS system needs only a small percentage of process water that competing algae growing systems require. This feature is explained in earlier portions of this document.

One other unique benefit of the PAGS process is that algae could be grown in a true mixotrophic mode. This means that simple carbohydrates could be used during the non-daylight hours and biomass production would increase accordingly. The only additional system required would be a simple agitated holding tank and pump to introduce the carbohydrate into the existing surge tank. This system is shown in summary form in FIG. 12 and would add less than 2% to the capital cost of a standard PAGS unit. The features of the PAGS system of high turnover, efficient mixing, etc. would all positively affect the mixotrophic mode as well.

Other mode of operation of PAGS.

The PAGS process is very robust and flexible. With this as a tool one is able to take advantage of the many processes and traits that micro algae employ in their inherent makeup. For convenience we have organized these applications into areas which appear attractive because of upcoming political events or trends that would make these applications attractive. These general classes of applications include: Metals Recovery from Interim Processes and Waste Streams, $CO_2$ Sequestration from large Industrial Point Sources, Valuable Materials that are now or can be produced by Micro Algae and Waste Water Treatment System Augmentation.

Metals Recovery from Interim Process and Waste Streams

Recovery of uranium from native phosphate ores. It is widely known that uranium occurs in all phosphate rock deposits. These uranium concentrations range between 50 and 200 parts per million in the ore deposit. A typical phosphate rock processing operation (normally phosphoric acid is the wanted product) would handle, even at today's depressed uranium prices somewhere in the range of $50,000,000 of uranium per year. The overall uranium in phosphate rock is in excess of the current known world reserves. Certain species of algae have an affinity for metal ions, particularly if they exist in the +2 valence state. The wet process for making phosphoric acid involves leaching of the rock with strong mineral acid and the uranium is found in solution as $UO_{2++}$ (known as uranyl ions). This state or condition of the uranium would favor the adsorption of the uranyl ion by micro algae on their polysaccharide outer layers. Preliminary testing would indicate that the algae could "hold" as much as 500% of their own dry weight for something with the atomic weight of uranium. Using the above information, a typical phosphate rock processing operation could utilize a few million pounds of microalgae per year to recover the majority of this now wasted resource. Required modifications to the PAGS process are very minor for this application as the algae could be used in a relatively dilute (1-10 grams per liter) concentration and the algae need not be alive for the adsorption process to occur. Final conversion of the adsorbed uranium to the current market composition ($U_3O_8$ or yellow cake) could be a plasma torch system which is currently available and used for waste disposal and metal recovery processes.

Recovery of Rare Earth elements. Rare Earth elements are the lanthanides (atomic number 57 through 71) and are relatively common in the earth's crust. Most are more common than element iodine which is used as a household antiseptic. They are receiving interest because of their use in the semiconductor industry, powerful magnets, communication devices and etc. The major commercial source today is China because their extraction and purification produces toxic waste streams and by products. Rare Earth elements exist in the coal found in the Appalachian Mountains. They are also candidates for microalgae adsorption and recovery and the PAGS process could be used here in conjunction with a facility that pulverized coal. Pulverized coal would be an easy candidate for mineral acid leaching that would convert the Rare Earth metals to a positive ion. The concentration required for the microalgae is relatively low and, as above, the algae need not be alive to perform this function. It is an adsorption process where the metal ion adheres to the "sticky" polysaccharide coating of the algae.

Political events may require that a source other than China is needed for these high value materials and a modification to the PAGS process could be used at an existing facility that currently ignores the Rare Earth materials present in the coal which is combusted as fuel.

Recovery of Radioactive Nuclides. These are normally products of the fission process used for electrical power generation from nuclear reactors. Typically, they are isotopes of elements that have a half-life of 1-10,000 years and are cancer causing in most mammals, including humans. In the case of the Fukushima disaster in Japan some 100,000,000 tonnes of water containing isotopes of cesium, strontium and plutonium were created. The concentrations of these materials in the water are quite low but beyond the safe limits for simple disposal. Algae could be used to capture these materials by providing a volume where the algae concentration is quite high (perhaps 10,000,000 cells per mL) and the adsorption process would bioaccumulate these materials. The radioactive materials still exist but in a much smaller volume that could be contained for the periods required. A PAGS facility proximate to the disaster site could function for a period of time required to process the contaminated water (perhaps 1-2 years). The problem still remains regarding the ultimate fate of the materials but the volumes involved are much more manageable.

$CO_2$ Sequestration from Large Industrial Point Sources Carbon Dioxide is likely to receive more attention if the planet continues to warm with the attendant problems caused by the greenhouse gas. A likely target for reducing the emissions will be large industrial facilities that produce a high concentration of $CO_2$ in their effluent gas. This high concentration would be attractive as a feed stock for a PAGS facility. This wastestream (which could become a cost for the producer) would be ideal feed stock for growing algae and likely could be obtained at zero or perhaps even negative costs. Candidate processes that currently fit these criteria are listed in Table 4 with estimated world effluent values.

The PAGS system would capture 90%+ of the $CO_2$ and convert it into biomass which at a typical industrial installation would result in a commodity type material that could be sold for various uses.

Valuable Materials that are now or can be produced by Micro Algae

This class of materials can largely be described as niche or high value items that function as nutraceuticals, active pharmaceutical ingredients, cosmetic components or other high value items. Typically, these materials (the active ingredient) have retail selling prices of $10,000-$100,000 per kilogram. Many of these items are known to exist in small concentrations for specific micro algae species. The problem to date is being able to obtain these microalgae species in the purity levels needed for component extraction and further processing. Typically, the worldwide market for these materials is quite small; somewhere between 1-100 tons per year. As an example one material could be a tocopherol like material. Tocopherol (or vitamin E) is a complex molecule with 4 asymmetric carbon sites. This would yield as many as 16 optical isomers and perhaps 8 have been studied in some detail. Tocopherol can be made synthetically but the isomers found differ from the natural material which may start in soybeans. This confirms out that Nature's laboratory operates differently than ours and the materials produced naturally could be different and have higher values or selling prices. This is true for the many products that could be obtained from microalgae and these would be quantified once a reliable quantity of specific microalgae could be obtained at a predictable cost. PAGS is designed to satisfy such criteria.

Waste Water Treatment System Augmentation

Waste Water Nutrient Removal. Microalgae need both phosphorus and nitrogen to maintain their growth and reproduction cycle. Currently the nitrogen and phosphorus have been identified as being largely responsible for the Chesapeake Bay's reduction in crustaceans, shellfish and sport fish populations. It has been demonstrated that micro algae can be used to reduce the concentration of nitrogen and phosphorus down to very low levels. The process required converting a portion of the existing wastewater stabilization ponds into volumes of very high algae concentration. This was done by using a PAGS type algae growing system and a cross flow filtration system which concentrated the algae and produced a very clean permeate. This permeate was suitable for release into the Pacific Ocean or almost any other water body. The PAGS process needed no modification except the expansion in capacity of the dewatering system. In this instance, the permeate from the dewatering system was the industrial facility's waste water stream. The PAGS process provided robust healthy algae that acted as a continual seed stock while most of the nitrogen and phosphorus assimilation was done by algae recycled from the growing volumes. Surplus algae (you do not need to recycle the total produced) can be converted to various saleable by products.

Fracking Water Cleanup.

The water employed in the fracking process will contain many heavy metals and materials that are not suitable for release into local rivers and estuaries. Microalgae will have a place in the concentration and collection of these as yet undefined materials. Typically, it takes several years for the regulatory statutes to respond to new materials that appear in waste streams. The PAGS process will likely have application here as a solution to an ongoing waste treatment problem.

EXAMPLES

Certain embodiments of the invention will not be described in more detail through the following examples. The examples are intended solely to aid in more fully describing selected embodiments of the invention, and should not be considered to limit the scope of the invention in any way.

Example 1—One Set Up and Operation Mode of the Photosynthetic Algal Growth System (PAGS) of the Current Invention The PAGS microalgae growing system as diagramed in FIG. 1 has the following capabilities:
1. The system is closed to the outside environment preventing intrusion by predators and other alien bodies.
2. The system is also under positive pressure to ensure the system "leaks out" similar to the production of active pharmaceutical ingredients. The starting materials are known and free from unwanted items that cause contamination.
3. The system is expandable and economies of scale can be realized. This means large central utility systems and supporting functions. The actual growing system is modular and expandable based on specific customer requirements.
4. The system is robust and can function on a 24/7 basis. Typically, this would mean microalgae growing in the day and harvest at night. Capital costs for the required ancillary processing equipment dictate high utilization factors.
5. The system is designed with an eye to total operation. This means consideration of the transients (start up and shut down). Operating mode, in-situ repair during operation and tolerance of catastrophic events (major failure or operator error).
6. The system provides optimum microalgae growing conditions. These will be influenced by the diurnal cycle through ambient temperature, light concentration and nutrient needs.

The above items are discussed in more detail below:
1. Closed System—The system is essentially air tight and the known (or designed) leakage points will be maintained and monitored. In our system this feature will be provided by a sterile nitrogen blanket that operates continuously.
2. Starting Materials—All the starting (raw) materials are of known and approved constituents. This includes the process water, recycle water, algae seed stock, micronutrients and the nitrogen blanket gas. This would permit utilizing such capital cost saving features as cast iron pumps (with purified process water as the sealing material) and similar standard or commodity items.
3. Economies of Scale—The system shares utilities and support functions with other algae growing modules. An algae growing module (as presently envisioned consists of 10 100-meter long polymeric plastic tubes of 100 mm diameter. Additional modules could be added as customer requirements dictate. Also extending the tube lengths up to a factor of 10 are possible if required for production.
4. Robustness—The system operates with some margin of safety. The required light transmission, tensile strength and extrudable characteristics of the plastic chosen for construction. Early experimental work has concluded that polyurethanes have the best blend of characteristics for the actual tubes. The diameter of the microalgae growing tube is about 100 mm. This would seem to best utilize the available light conversion to biomass. These functional criteria include:
    a) Extrudable Material (long runs with minimal connections)
    b) High Tensile Strength (see FIG. 5)
    c) High Light Transmissivity (>90%)
    d) High ultraviolet light tolerance (resists yellowing and strength loss)
    e) Customizing Capability (flexibility enhanced with polyol selection etc.)
    f) Limited for toxic additives (phthalates etc.)
5. Total Operation—The system is designed for total operation. Considerations include:
    a) Start Up—A small volume is required which can be expanded incrementally (by opening valves) maintaining good algae concentration for growth.
    b) Operation—Growing during the day, harvest at night, the surge tank volume merely reduces maintaining algae concentration promoting consistent dewatering/concentrating activities.
    c) Day/Night Operation—Once day light is no longer available, the oxygen product may cause the pH in the system to rise suppressing later (the next day) growth. Nitrogen is sparged in the surge tank and oxygen is removed as it is generated, thereby increasing growth rate. This eliminates slow growth start up the next day.
    d) Cleaning/Species Change—The system is designed for in situ cleaning (by chemicals) and free draining. Flows can be increased to allow scouring of the system and minimal residual contamination.
    e) Optimal Growth Conditions—The system is designed to control temperature and process conditions. The temperature is controlled by:
        Cooling (nitrogen sparge and subsequent water evaporation)
        Heating (polypropylene glycol/water in tank jacket)
It should be noted that every algal species likely has optimal process conditions and nutrients and other additives can be introduced as needed.

Process Water System

The process water system is the heart of the microalgae growing system and diagramed in FIG. 7. It prevents contamination of the system by presenting a water of known cleanliness to contact the algae. This is done using a water filter system followed by an ultraviolet light sterilizer. Typically, the filtration system includes the following:
    A coarse filter with a maximum particle flow permission limit of no more than 5 microns;
    An activated charcoal filter to remove any organic material or halogen ion that might exist in either the source water or the recycled water from subsequent operations;
    A fine filter with a maximum particle flow permission limit of no more than 0.35 microns;
    An ultraviolet light sterilizer to destroy any spores or bacteria that might get through the filtration system. The sterilizer has a minimum exposure capability of exposing the water to 30 watts per gallon per minute to ensure sterility.

The system operates continuously and is installed in a duplex mode (installed back up). This is analogous to a boiler operation which nearly always has two source pumps to ensure the boiler has 24/7 capability. The filters have bypass capability which allows the cartridges to be exchanged while the system is operating.

Any "new or recycled" water which is introduced to the system must first go through the above process before reaching the surge tank which provides a clean ample water source for the process.

Nitrogen System—The nitrogen system has two major functions and is diagramed in FIG. 8. It provides a sterile blanket under positive pressure to the entire microalgae growing system and provide cooling capability by the evaporation of water by the sparging operation in the microalgae growing surge tank. During the sparging operation product oxygen is also removed which speeds up the overall photosynthesis process. The nitrogen would likely be stored at a proximate tank where the nitrogen is likely liquid. This material would have been produced via a cryogenic distillation process and would be very pure and sterile. As backup a sterile filter would be included before the nitrogen is introduced to the microalgae growing process. The sterile filter would be provided in a duplex mode (an installed spare) to ensure that all the nitrogen gas is of suitable quality for the growing process. Similar care would be taken if ambient air is used.

Gaseous $CO_2$ Feed System—$CO_2$ is the normal food for microalgae. This $CO_2$ (in nature) is present in the ambient air at a concentration of about 400 parts per million. The $CO_2$ is soluble in water and dissolves following the principles outlined in Henry's Law. Therefore, the growth rate of the microalgae is dictated by the mass transfer rate of $CO_2$ from ambient air into the water where it is dissolved and the microalgae assimilate this into resulting biomass.

The PAGS process intends to make the rate limiting step the actual ability of the microalgae to assimilate the $CO_2$. Therefore, ample $CO_2$ must be present in a dissolved form. The mechanism for this involves:

Introducing the pure (or nearly so) $CO_2$ as very fine/small bubbles which have an extremely high surface area to contained volume ratio (units of inverse length). We have chosen to adapt a novel nanobubble generator for this purpose (see FIG. 9).

Operating the system at much higher than ambient pressure; higher pressure increases the $CO_2$ dissolving rate as well as increasing the amount of $CO_2$ the water will accept.

Many existing microalgae growing systems use a mixture of air and $CO_2$ as a feed material. The rationale behind this is to mimic the low level of $CO_2$ (400 ppm) which nature uses. The down side of this is the companion air with the $CO_2$ actually strips some wanted material out. This process is common if you want to remove oxygen from a liquid stream; just bubble a surplus of nitrogen through it. PAGS uses a high content $CO_2$ gas and forces the limiting step to be the actual assimilation process (or the reaction kinetics). Almost all existing industrial processes are limited by either mass or heat transfer system capability. This feature will improve our unit volume productivity and overall yield.

The $CO_2$ used in any microalgae growing process must be free of heavy metals or other contaminants that could be toxic to the actual algae or the downstream products that may be created. Therefore (depending on the actual source) the characteristics of the $CO_2$ must be known fully and be reliable.

Dewatering System

Microalgae will be grown in the PAGS operation at a concentration of about 0.5 grams of biomass per liter of water or media. Most customers will desire this biomass to contain much less water than the above amount. Hence our "standard" system will have the capability to concentrate the biomass by a factor of 20 which will yield a "thick" paste like material which is still transferable by standard pumps and not significantly damage or degrade the biomass. Our standard system is a cross flow filtration operation (FIG. 10) which has the following advantages:

There is no "dead end" step where a filter cake accumulates and must be periodically removed (normally by hand and is a tedious job)

The permeate (removed water) is almost totally free of suspended solids. This is recycled to our source water treatment system for reuse. The recycled water also carries valuable concentrations of dissolved nutrients which are recycled and converted into biomass in later operation.

These cross flow filters were developed for the pharmaceutical industry (vaccine purification) and they are designed for small hydraulic diameter body removal. These devices have been modified by others to accept the industrial scale of operation.

Seed Stock and Nutrient Introduction System—The microalgae growing system will need initial seed stock and periodic infusion of micro-nutrients. These will be algae seed stock and nitrogen and phosphorus containing compounds. These materials will be produced and formulated off site and introduce via a metering pump into the surge tank of the microalgae growing system as shown in FIG. 11. Initially, the seed stock will be introduced with a relatively small "heel" (residual volume) in the tank to minimize the potential for over dilution. This over dilution would require additional time (and risk) for the algae to reach a healthy and reproductive state. The microalgae growing system is designed for step wise volume expansion such that the initial inoculation volumes required are relatively small and the system evolution can be controlled by valves which cause additional growing volumes to become active.

The nutrients are nitrogen and phosphorus containing compounds and perhaps even various vitamin-like substances which may be required. They will be introduced via metering pumps and ongoing concentrations will be continuously monitored. These materials will be available to the algae growing process such that optimum growth rates can be maintained. The PAGS growing operation has very quick response times and turbulence is very high which maintains consistent and uniform concentrations.

Example 2—Running PAGS Process as a Metals Recovery from Interim Processes and Waste Streams Metals Recovery from interim Processes and Waste Streams, the PAGS process functions to produce a sacrificial stream of microalgae which is introduced to a highly acidic (low pH) stream. The contact time required here is about 15 minutes and the concentration of algae needs to be in the range of 5-50 million cells/mL (this is perhaps a solids concentration of 0.05-0.5 grams per liter) of process solution depending on the hydraulic diameter of the specific algae used. The contact volume would be operated as a simple continuously flow stirred tank reactor (CFSTR or backmix system) and the incoming algae would need to be at a higher concentration than the required concentration in the reactor.

For an industrial application such as the phosphate rock uranium recovery system, the active volumes here would quite large, but efficient pulsed gas mixing or other alternatives could be used. Light is not required for the algae so the physical dimensions of the volume are not constrained. The PAGs system would be run as described in Example 1 but the outlet stream from this operation would need to be further processed to remove the water and convert the final metal product (in this case uranyl ions) into the final commodity product U308 or yellowcake; but this is independent of the PAGS process.

Example 3—Using the PAGS System for $CO_2$ Sequestration from Large Point Sources $CO_2$ Sequestration from large Point Sources would require the number of PAGS modules to be quite large. This is because for a typical industrial facility, such as a direct iron ore reduction facility, that may produce about 1,000,000 tons of iron per year. The $CO_2$ produced here is about 90% of the product by weight which yields an instantaneous rate of 30,000 cubic feet per minute of $CO_2$ gas. This gas would be present at about 28% by volume in the facility's effluent. For this application the PAGS system would be run as in Example 1 but requires the PAGS nanobubbler system to be upgraded to accept these volumes. Also if it is desired that all the $CO_2$ be processed or converted an LED or other artificial light system would need to be added to PAGS for operation in non-daylight hours. Also the PAGS dewatering system would need to be expanded to accept the large volumes of algae media that would need to be processed. The PAGS process is uniquely qualified for this application because of:

The nearly total recycle or capture of the water used
The efficient use of the required nutrients
The high utilization of the $CO_2$ These advantages are compared to existing competing alternatives and the fact that many of these facilities (like direct iron direct reduction) are located in arid regions where process water is expensive or nonexistent.

Example 3—Production of High Value Products Such as Astaxanthin in the PAGS System Production of astaxanthin or other valuable materials already produced by microalgae (such as the phycobiliproteins or sporopolinin) are made in the PAGS system as described in Example 1. Essentially no modifications are required in the PAGS facility other than to install downstream processing for extraction of astaxanthin. This easy shift to production of valuable products already produced in microalgae is due to the basis for design and other applications were included in the modular addition concepts employed. This market could be quite large as currently many niche products are known to be contained in microalgae. They have not been developed because a reliable and economically competitive process for producing the algae is currently not available.

Example 4—Waste Water Treatment System Augmentation Using PAGS

Waste Water Treatment System Augmentation is easily done using the PAGS system as described in Example 1 with the exception of the sourcing of the water used to make up the algal growth medium. The PAGS facility produces robust microalgae feed stock or seeds that act as the parents to micro algae in a volume of the existing waste water treatment system that has a very high microalgae content. This high content of microalgae allows them to scavenge the nitrogen and phosphorus (nutrients) in the wastewater to actually become part of the biomass. This is later recovered and converted to many potential economic uses. The required modifications to the PAGS facility are:
1. A larger dewatering system as the clear permeate here actually becomes the existing facility's treated wastewater stream.
2. An additional gas handling system that could be used to mix the volumes required for the actual assimilation of the nitrogen and phosphorus values in the wastewater.
3. A water handling system that would be used to transport the algae containing media from the existing modified waste water treatment system to the dewatering operation.

No changes in the operation of the PAGS system are required.

Definitions

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

"Microalgae" have been variously defined through the ages and it is prudent to describe the microalgae to which this invention could apply. For the purposes of this invention, microalgae include the traditional groups of algae described in Van Den Hoek et al. (1995). This invention can be used in the photosynthetic and mixotrophic culturing of microalgae.

"Phototrophic" and "photoautotrophic" are used interchangeably and refer to growth on simple medium without the use of fixed organic carbon, all carbon is supplied by inorganic carbon (e.g., carbon dioxide, bicarbonate, or carbonate).

"Mixotrophic" growth is growth in the presence of a fixed carbon source in the light with inorganic carbon also present where improved productivity is achieved due to the presence of the fixed organic carbon.

"Photobioreactor" is a system where a photosynthetic organism is capable of carrying out photosynthesis due to the design of the system (allowing exposure to light and control of conditions to allow cell growth amenable to photosynthesis.

Light reaction chamber" is a section of a device where photosynthesis is allowed to proceed.

Reynold's Number" is a dimensionless ratio of the inertial energy divided by the viscous dissipation energy and it is now believed that a value of 2100 would represent turbulent flow which has not been rigorously defined by analytical techniques. Basically, you use experimental data to define required system drops, etc.

The term "self-shading" refers to the reduction of light available to specific algae cells due to the presence of other algae cells through which the light must pass prior to hitting the algal cells of interest. As a population phenomenon, "self-shading" has the effect of limiting the maximum potential culture cell density by restricting the light available to the average cell in the culture. Often this is referred to as "self-limiting" or "light limited" cultures which, for the purposes of this application will be considered equivalent terms.

The microalgal growing system and its associated methods are collectively and individually referred to herein as the "Pure Algae Growth System" or "PACS" which are used interchangeably in this application.

The pure algae growth system of the present invention is for feeding a plurality of input materials and for generating pure algae there from. The feeding of the input materials and the generating of the pure algae is done in a safe, convenient, and economical manner. In the system of the present invention, first provided is a primary tank for receiving the plurality of input materials, for mixing the plurality of input materials, and for dispensing as output material the input materials after mixing. The primary tank has an upper extent with a top. The primary tank has a lower extent with a bottom. The upper extent is in a cylindrical configuration with a vertically oriented upper axis. The lower extent is in a geometric configuration with a vertically oriented lower axis coextensive with the upper axis. The plurality of input materials includes an algae feed stock supply with an algae feed stock input line coupling the algae feed stock supply to the top of the primary tank. The plurality of input materials also includes a micro-nutrient supply with a micro-nutrient input line coupling the micro-nutrient supply to the top of the primary tank. The plurality of input materials also includes a cleaning solution supply with a cleaning solution input line coupling the cleaning solution supply to the top of the primary tank.

Next provided is a sterile gas supply. A sterile gas supply input line couples the sterile gas supply to the top of the primary tank.

Next, a heating/cooling fluid supply is provided. A heating/cooling fluid supply input line couples the heating/cooling fluid supply to an intermediate extent of the primary tank and passes through the primary tank for temperature control purposes.

Next provided is a carbon dioxide supply. A carbon dioxide supply input line couples the carbon dioxide supply to a primary location following the primary tank.

A raw water supply is next provided. A raw water supply input line couples the raw water supply to a secondary location following the primary tank.

Next, a plurality of output stations are provided. Included are a vent to atmosphere station, a heating/cooling media return station, a cleaning disposal station, and an algae concentrate/product station.

The vent to atmosphere station includes a vent to atmosphere output line. The vent to atmosphere output line couples the top of the primary tank to the vent to atmosphere station for disposing of gasses formed in the top of the primary tank.

The heating/cooling media return station includes a heating/cooling media output line. The heating/cooling media couples the heating/cooling media input line to the heating/cooling return station for controlling the temperature in the primary tank.

The cleaning solution disposal station includes a cleaning solution disposal output line. The cleaning solution disposal output line couples the bottom of the primary tank and the cleaning solution disposal station. The cleaning solution disposal line includes a pump followed by a nano bubbler at the primary location followed by an algae growing system.

The algae concentrate/product station includes an algae concentrate/product line between the bottom of the primary tank and the algae concentrate/product station. An algae dewatering system is provided in the algae concentrate/product line. A water return line couples the algae dewatering system and a water treatment system at the secondary location.

Next provided in the system is at least one first tube with an associated return second tube. The at least one first tube and the return second tube are transparent for the visible treatment of algae passing there through.

The nano bubbler and the algae growing system and the algae dewatering system constitute a module. The system includes at least one module.

Lastly provided in the system is a solids weigh system and feeder operatively coupled between the micro-nutrients supply and the primary tank.

The flow of material through the algae growing system is turbulent with a Reynolds Number of 10,000, plus or minus 20 percent.

The present invention includes a pure algae growth method for feeding a plurality of input materials and for generating pure algae there from. The feeding of the input materials and the generating of the pure algae are done in a safe, convenient, and economical manner. The method includes the following steps.

The first step is providing a primary tank for receiving the plurality of input materials, for mixing the plurality of input materials, and for dispensing as output material the input materials after mixing. The primary tank has an upper extent with a top. The primary tank has a lower extent with a bottom. The upper extent is in a cylindrical configuration with a vertically oriented upper axis. The lower extent is in a geometric configuration with a vertically oriented lower axis coextensive with the upper axis.

The next step is providing the plurality of input materials including an algae feed stock supply with an algae feed stock input line coupling the algae feed stock supply to the top of the primary tank. The plurality of input materials includes a micro-nutrient supply with a micro-nutrient input line coupling the micro-nutrient supply to the top of the primary tank. The plurality of input materials includes a cleaning solution supply with a cleaning solution input line coupling the cleaning solution supply to the top of the primary tank.

The next step is providing a sterile gas supply with a sterile gas supply input line coupling the sterile gas supply to the top of the primary tank.

The next step is providing a heating/cooling fluid supply with a heating/cooling fluid supply input line coupling the heating/cooling fluid supply to an intermediate extent of the primary tank and passing through the primary tank for temperature control purposes.

The next step is providing a carbon dioxide supply with a carbon dioxide supply input line coupling the carbon dioxide supply to a primary location following the primary tank.

The next step is providing raw water supply with a raw water supply input line coupling the raw water supply to a secondary location following the primary tank.

The next step is feeding the plurality of input material to the primary tank.

The next step is providing a plurality of output stations including a vent to atmosphere station, a heating/cooling media return station, a cleaning disposal station, and an algae concentrate/product station.

The next step is including in the vent to atmosphere station a vent to atmosphere output line coupling the top of the primary to the vent to atmosphere station for disposing of gasses formed in the top of the primary tank;

The next step is including in the heating/cooling media return station a heating/cooling media output line coupling the heating/cooling media input line to the heating/cooling return station for controlling the temperature in the primary tank;

The next step is including in the cleaning solution disposal station a cleaning solution disposal output line coupling the bottom of the primary tank and the cleaning solution disposal station, the cleaning solution disposal line including a pump followed by a nano bubbler at the primary location followed by an algae growing system.

The next step is including in the algae concentrate/product station an algae concentrate/product line between the bottom of the primary tank and the algae concentrate/product station, an algae dewatering system in the algae concentrate/product line, a water return line coupling the algae dewatering system and a water treatment system at the second location.

The final step is feeding the output stations from the primary tank.

Alternatively, the method includes the step of feeding algae feed stock to the tank in the absence of a sugar solution to achieve phototropic algae growth.

Also alternatively, the method includes the step of feeding a sugar solution to the primary tank in the absence of algae feed stock and visible radiation to achieve photographic algae growth.

For operating the system in non-daylight hours, the carbon dioxide source is removed and replaced by a feed to the tank of sugar, preferably an aqueous solution.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A continuous method for growing a specific strain or species of micro algae, the method adapted to operate under positive pressure causing internal high turbulence, which reduces contaminant intrusion, the method also being capable of providing growing conditions for microalgae and recycling unused reactants and process water in a growth system, the method comprising the steps of:
   a) providing the specific strain or species of micro algae;
   b) providing a central distribution tank adapted to act as a central process control location for the growth system where all process variables are monitored and data is sent to a central computer system which maintains the growing conditions;
   c) introducing the specific strain or species of microalgae into the central distribution tank;
   d) providing a plurality of microalgae growing modules, adapted to function in a true mixotrophic manner allowing full 24/7 growth cycles and an attendant high growth rate, wherein the microalgae growing modules are made of a material comprising a polyurethane polymer which is resistant to ultraviolet degradation from sunlight and which can be fabricated in lengths exceeding 200 meters without the need for connectors and having reduced biofilm buildup due to the internal high turbulences, which scour the interior surfaces;
   e) providing a source of pressurized $CO_2$, connected to the a central distribution tank for pressurizing the $CO_2$ supply, wherein the $CO_2$ supply is introduced at a pressure sufficient to cause a turbulent flow within the growth system;
   f) repairing and installing additional units while the growth system is growing algae, wherein the microalgae growing modules have a diameter sufficient to provide required tensile strength, specific volume and sunlight transmission;
   g) providing an inline dewatering system which allows algae harvesting while the growing system is functioning thereby maintaining algae growing concentrations during the growth cycle;
   h) recovering and utilizing unused reactants and process water, wherein such unused reactant and process water are reconditioned to defined specification prior to reuse;
   i) adjusting the temperature of the material in the algae growing modules, wherein the growing modules comprise growth medium, wherein the growing modules are connected to the central distribution tank via transfer lines, and wherein the temperature adjustment, either hotter or colder, is done using a liquid material not toxic to the growing algae but which never actually is in physical contact with it, the required heat transfer being accomplished via a tank jacket on the central distribution tank or external heat exchanger placed in the growth medium transfer lines;
   j) providing a physically smooth internal construction within the growth system having minimal locations for material to lodge, thereby permitting the use of Clean In Place technology to thereby allow system cleaning and purification to be accomplished without system disassembly and reassembly;
   k) providing support systems that can add required micronutrients, food for the algae, or other materials required for optimal algae growth, wherein the required micronutrients are added to the central distribution tank;
   l) maintaining the specific strain or species of microalgae in the growth system and exposing same to a light source or source of sugar for sufficient time for growth of the algae to reach about 0.5 grams of biomass per liter of water or media;
   (m) removing the biomass from the growth system and removing excess water or medium from the biomass by moving the biomass through a filtration system, thereby providing the pure specific strain or species of micro algae, and
   (n) cleaning the growth system by introducing a cleaning solution into the central distribution tank without disassembly and reassembly of the growth system to provide a clean growth system for reinoculating the growth system with the previous algae or for introducing a different algae species and repeating steps (a) to (m).

2. A continuous method for growing a specific strain or species of microalgae while reducing contaminant intrusion, the method comprising the steps of:
   (i) providing the specific strain or species of micro algae and introducing same into a closed and positive pressurized growing system, wherein the growing system is continuous with an in situ cleaning functionality and comprises:
   (a) a central distribution tank comprising a temperature controlling jacket and acting as a central process control location, wherein growth and process variables are controlled, micronutrients supply nitrogen and phosphorus, sterilized inert gas acts as a blanket to block intruding species, and sterilized water and $CO_2$ are supplied;
   (b) a computer system communicatively connected to the central distribution tank for monitoring the process variables and for modulating them to maintain growing conditions;
   (c) a plurality of microalgae growing tubular modules communicatively connected to the central distribution tank and positioned for exposure to a light source, wherein the microalgae growing tubular modules are fabricated of a translucent or transparent polyurethane polymer resistant to ultraviolet degradation and fabricated in continuous lengths of about 100 meters, wherein the microalgae growing tubular modules have a diameter for maintaining tensile strength, movement of a specific volume of microalgal culture and light exposure;
   (d) a pressurized pumping source connected to the central distribution tank for pressurizing the growth system, wherein the internal pressure of the growing system is at a pressure sufficient to cause a turbulent flow within the growing system and minimize the accumulation of biofilms in the microalgae growing tubular modules;

(e) a nano-bubbler positioned between the pressurized pumping source and microalgae growing tubular modules, thereby providing and producing bubbles of $CO_2$ for increased solubility of $CO_2$ in the growing system;

(f) an inline dewatering system comprising a filtration system which allows algae harvesting while the growing system is functioning, thereby maintaining algae growing concentrations in the growing system;

(g) a temperature adjusting system communicatively connected to the jacketed central distribution tank to maintain a growth temperature in the growing system;

(h) a venting system attached to the central distribution tank to remove unwanted gasses formed in the growing system; and (i) an inline recovering system for capturing unused reactants and process water, wherein such unused reactant and process water may be recycled;

(ii) maintaining the specific strain or species of micro algae in the growing system for sufficient time for growth of the algae to reach and maintain about 0.5 grams of biomass per liter of water or medium;

(iii) removing the biomass from the growing system and removing excess water or medium from the biomass by moving the biomass through the filtration system, thereby providing the specific strain or species of micro algae; and (iv) cleaning the growing system by introducing a cleaning solution into the central distribution tank without disassembly and reassembly of the growing system to provide a clean growing system for reinoculating the growth system with the previous algae or for introducing one or more different algae species and repeating steps (i) to (iii).

3. The method of claim 2, wherein the growing system functions in a mixotrophic manner and provides a 24/7 growth cycle.

4. The method of claim 2, wherein the microalgae growing tubular modules have a diameter of about 100 millimeters.

5. The method of claim 2, wherein the growth system further comprises an inlet for introducing an aqueous sugar solution for growth during non-daylight hours.

6. The method of claim 2, wherein the turbulent flow causes a scouring effect on the internal surfaces of the growing system, thereby minimizing accumulation of a biofilm and blocking of required light.

7. The method of claim 2, wherein the applied pressure ensures that any transfer of materials or gases is out of the growing system, thereby reducing the chance of contamination.

8. The method of claim 2, wherein the temperature is maintained by introducing a mixture of water and polypropylene into the temperature controlling jacket of the central distribution tank.

9. The method of claim 2, wherein the translucent or transparent microalgae growing tubular modules and turbulent flow allow the microalgae to spend sufficient exposure time in the light source.

10. The method of claim 2, wherein the turbulent flow within the growing system has a flow rate greater than a Reynolds Number of 10,000.

11. The method of claim 5, further comprising introducing a sugar solution into the growth system when exposure to the light source is reduced.

12. The method of claim 2, wherein the internal pressure in the growth system is about 2 Bars.

13. The method of claim 2, wherein the plurality of micro algae growing tubular modules is 10.

14. The method of claim 2, wherein the translucent or transparent polyurethrane polymer contains no phthalates.

* * * * *